(12) United States Patent
Potyrailo et al.

(10) Patent No.: US 7,524,455 B2
(45) Date of Patent: Apr. 28, 2009

(54) METHODS FOR DEPOSITION OF SENSOR REGIONS ONTO OPTICAL STORAGE MEDIA SUBSTRATES AND RESULTING DEVICES

(75) Inventors: Radislav Alexandrovich Potyrailo, Niskayuna, NY (US); Marc Brian Wisnudel, Clifton Park, NY (US); Scott Martell Boyette, New Hope, PA (US); Andrew Michael Leach, Clifton Park, NY (US); Kasiraman Krishnan, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 826 days.

(21) Appl. No.: 10/723,536

(22) Filed: Nov. 24, 2003

(65) Prior Publication Data

US 2005/0112358 A1     May 26, 2005

(51) Int. Cl.
*G01N 33/00* (2006.01)

(52) U.S. Cl. .................. 422/57; 422/50; 422/68.1; 422/72; 422/99

(58) Field of Classification Search ............... 422/68.1, 422/82.05, 72, 50, 99, 57
See application file for complete search history.

(56) References Cited

U.S. PATENT DOCUMENTS

| | | | |
|---|---|---|---|
| 4,774,315 A | 9/1988 | Miller | |
| 5,028,690 A | 7/1991 | Gallucci | |
| 5,043,203 A | 8/1991 | Fyvie et al. | |
| 5,252,494 A | 10/1993 | Walt | |
| 5,356,668 A | 10/1994 | Paton et al. | |
| 5,644,017 A | 7/1997 | Drumright et al. | |
| 5,668,202 A | 9/1997 | Hirata et al. | |
| 5,892,577 A | 4/1999 | Gordon | |
| 6,327,031 B1 | 12/2001 | Gordon | |
| 6,342,349 B1 | 1/2002 | Virtanen | |
| 6,500,547 B1 | 12/2002 | Potyrailo | |
| 2002/0173040 A1 | 11/2002 | Potyrailo et al. | |

FOREIGN PATENT DOCUMENTS

| | | |
|---|---|---|
| DE | 39 38 598 | 5/1991 |
| DE | 40 13 713 | 10/1991 |
| EP | 0 236 768 | 9/1990 |
| EP | 1 189 062 | 3/2002 |
| WO | 98/12559 | 3/1998 |
| WO | 99/35499 | 7/1999 |
| WO | WO 00/14540 | 3/2000 |

OTHER PUBLICATIONS

USCD Scientists Develop Novel Way to Screen Molecules Using Conventional CDs and Compact Disk Players, Science and Engineering UCSD Press Release, Aug. 20, 2003.
La Clair, et al., "Molecular Screening on a compact disc," Org. Biomol. Chem. 2003, 1 (Advance Article) (Abstract).
La Clair, et al., "Molecular Screening on a compact disc," Org. Biomol. Chem. 2003, 1, (Advance Article) (Paper).
La Clair, et al., "Molecular Screening on a compact disc," Org. Biomol. Chem. 2003, 1:3244-3249.
International Search Report dated Apr. 6, 2005.

*Primary Examiner*—Sam P Siefke
(74) *Attorney, Agent, or Firm*—Andrew J. Caruso

(57) ABSTRACT

Methods for applying sensor materials to optical storage media substrates are disclosed. After exposure to a sample of interest, the resulting sensors may be read in optical storage media drives for quantitative analysis of physical, chemical and biological parameters of the sample.

20 Claims, 10 Drawing Sheets

METHODS FOR DEPOSITION OF SENSOR REGIONS ONTO OPTICAL STORAGE MEDIA SUBSTRATES AND RESULTING DEVICES

BACKGROUND OF THE INVENTION

This disclosure relates to methods for deposition of sensor materials onto optical storage media for the analysis of physical, chemical and biological species and sensors produced thereby for quantitation of volatile and nonvolatile compounds in fluids.

Quantitation of biological and chemical compounds and other parameters is typically performed using dedicated sensor systems that are specifically designed for this purpose. These sensor systems operate using a variety of principles including electrochemical, optical, acoustic, magnetic, and many other types of detection. See, e.g., Mandelis, et al., Physics, Chemistry and Technology of Solid State Gas Sensor Devices, Wiley (New York, N.Y.), 1993; Potyrailo, et al., "Optical Waveguide Sensors in Analytical Chemistry: Today's Instrumentation, Applications and Future Development Trends", Fresenius' J. Anal. Chem. 1998, 362, 349-373; Albert, et al., "Cross-reactive Chemical Sensor Arrays", Chem. Rev. 2000, 100, 2595-2626. Alternatively, a variety of colorimetric liquid and solid reagents are available to perform visual evaluation of color change. Kolthoff, "Acid-Base Indicators", The MacMillan Company (New York), 1937; "Chemical Detection of Gaseous Pollutants" Ruch, W. E., Ed., Ann Arbor Science Publishers (Ann Arbor, Mich.), 1968.

Previously, it has been suggested that CD/DVD drives can be used for conducting optical inspection of biological, chemical, and biochemical samples. However, in order to make these drives useful for detection of parameters not related to digital data stored on optical media, the optical system of the drives is preferably modified, in some cases by having additional optical detectors. See, e.g., U.S. Pat. No. 5,892,577.

As the use of CD/DVD drives has developed, the development of sensors in conjunction with optical storage media has also developed for use in the CD/DVD drives. For example, U.S. Pat. No. 6,327,031 discloses optical discs having a semi-reflective layer to reflect a portion of light to one detector and transmit a portion of light to another detector.

U.S. Pat. No. 6,342,349 describes another optical-drive-based measurement system. In this system, the analyte-specific signal elements are disposed within the optical storage media's tracking features. Thus, the analyte-specific signal elements are readable by the optics used for tracking, although modified or additional optics elements are added. For the system to be applicable, the signal responsive moiety is of a small size, compatible with the size of the focused light beam and is reflective. Most preferably, it is a gold microsphere with a diameter between 1 and 3 micrometers. Another method has been also described to screen the recognition between small molecule ligands and biomolecules using a conventional CD player. A procedure was developed to attach ligands to the reading face of a CD by activating the terminus of polycarbonate, a common polymer composite within the reading face of a CD. Displays were generated on the surface of a CD by printing tracks of ligands on the disc with an inkjet printer. Using this method, discs were created with entire assemblies of ligand molecules distributed into separate blocks. A molecular array was developed by assembling collections of these blocks to correlate with the CDROM-XA formatted data stored within the digital layer of the disc. Regions of the disc containing a given ligand or set of ligands were marked by their spatial position using the tracking and header information. Recognition between surface expressed ligands and biomolecules was screened by an error determination routine (see Org. Biomol. Chem., 1, 3244-3249 (2003)).

Deposition methods used for preparation of sensor regions and/or spots onto optical storage media include inkjet printing and robotic or manual drop addition onto the surface of the disc (U.S. Pat. No. 6,342,349), light directed synthesis of biological microarrays on the disc (International Patent Application No. WO 98/12559), and spotting of arrays on the disc (International Patent Application No. WO 99/35499). Analyte-specific reagents utilized in such sensor regions or spots can be arranged in arrays, for example, combinatorial arrays (International patent application WO 98/12559). In addition to the application of solid and gel types of analyte-specific reagents to discs, other types of reagents utilized in sensor regions/spots include liquid-containing reagents (see, Anal. Chem. 71, pp. 4669-4678 (1999).

For deposition of sensing spots onto optical storage media, it would be advantageous to apply these sensing spots in a highly reproducible manner and in well-defined locations. Improved methods for depositing such sensor spots onto optical storage media substrate are thus desirable.

BRIEF DESCRIPTION OF THE INVENTION

The present disclosure is directed to sensor devices and methods for making these sensor devices. The sensor devices include an optical storage media and a sensor film comprising a polymer support in combination with an analyte-specific reagent applied to at least a portion of the optical storage media. The polymer supports utilized in the sensor films can be selectively permeable to analytes on the basis of size, phase, solubility, and ion charge. In one embodiment the sensor film is applied as sensor spots to the surface of the optical storage media.

Methods for producing these sensor devices include selecting an optical storage media for use as a substrate, selecting a polymer support, adding an analyte-specific reagent to the polymer support to form a sensor film, and applying the sensor film to the optical storage media. In one embodiment, the sensor film is prepared and exposed to the analyte of interest prior to its application to the optical storage media.

BRIEF DESCRIPTION OF THE DRAWINGS

FIG. 4 is a depiction of one embodiment of the present disclosure, whereby a clear transparent film containing environmentally sensitive regions is deposited onto the whole surface of an optical storage media.

DETAILED DESCRIPTION OF THE INVENTION

Figure 1:
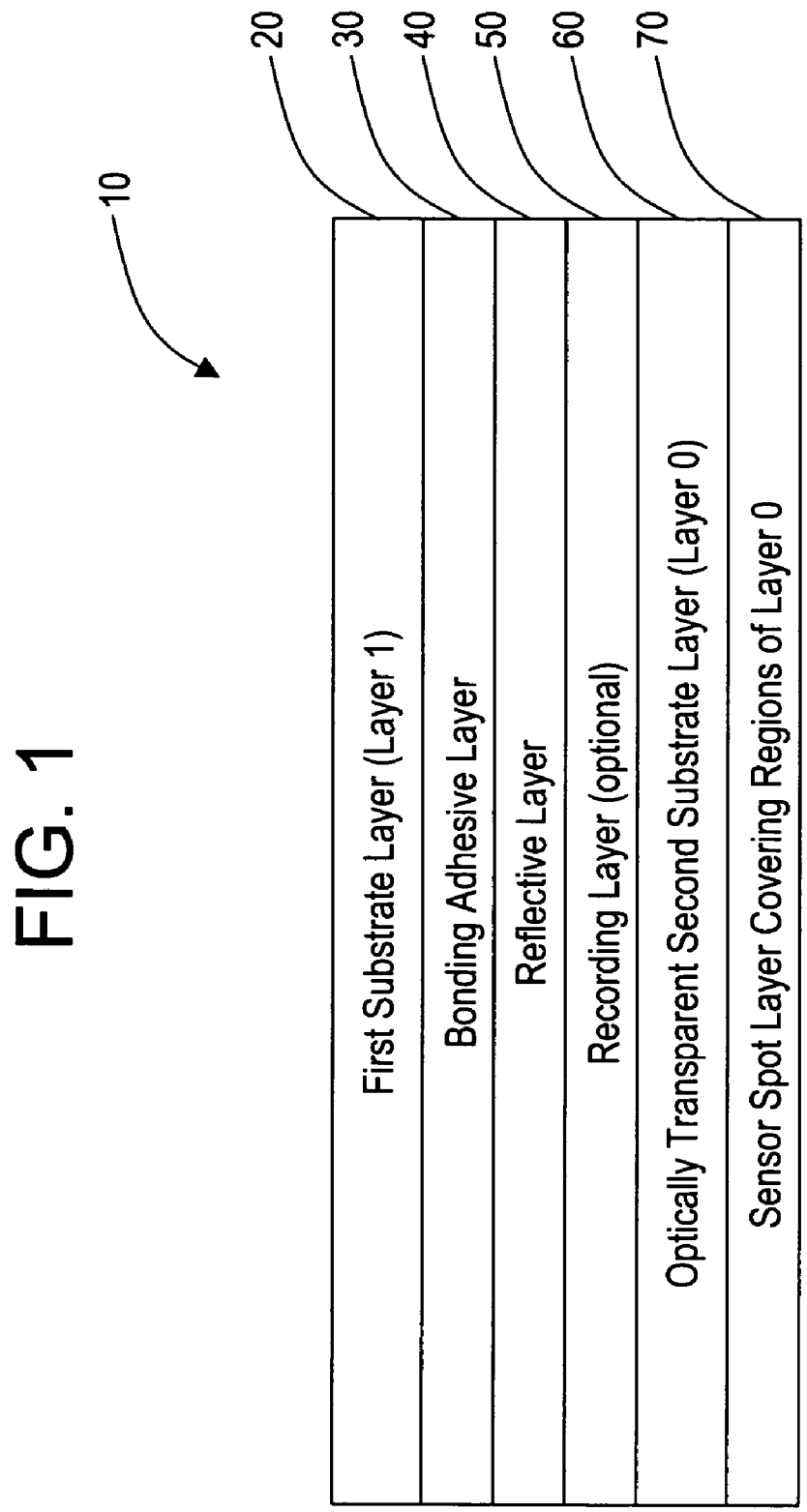
FIG. 1 is a graphical depiction of an optical storage media of the present disclosure possessing a sensor film.

The present disclosure is directed to methods for forming sensor devices readable in optical storage media drives for quantitative analysis of physical, chemical and biological parameters. Quantitative information is obtained about the chemically and biochemically-related changes of sensing materials deposited on an optical storage media. The present disclosure provides optical storage media having a sensor film or sensor layer applied thereto. As used herein, "sensor layer" and "sensor film" are used interchangeably.

Optical storage media have become widespread in audio, video, and computer data applications. Examples of optical storage media articles include, but are not limited to, optical discs such as CDs, CD-Rs, CD-RWs, DVDs, DVD-Rs, DVD-RWs, Blu-ray as well as any other optical storage media known in the art. Multi-layer structures like DVD-5, DVD-9, and multi-sided formats such as DVD-10 and DVD-18, and magneto-optical discs (MO) are also included. While the present disclosure is described below with reference to a compact disc (CD) and/or a digital versatile disc (DVD), the methods described herein may be practiced with any optical storage media.

In accordance with the present disclosure a substrate, i.e., an optical storage media, is initially provided. The optical storage media substrate may be of any type and should be encoded with information beforehand in the form of pits and/or a continuous groove on at least one side. Sensor substrates can be any commercial CD or DVD with any label on the reading or non-reading surface. If a label is present, the label can be of any color, transparent/nontransparent, etc. In addition, in accordance with the present disclosure, there is no need to have information on the optical storage media that matches or is in some way related to the placement of the sensor material on the disc. Any prerecorded information is sufficient to operate the sensor.

Typically, a CD is an injection-molded piece of clear polycarbonate plastic. During manufacturing, the plastic is impressed with microscopic bumps arranged as a single, continuous, extremely long spiral track of data. The spiral track of data circles from the inside of the disc to the outside. When the clear polycarbonate is formed, a thin, reflective layer (typically aluminum, silver or gold) is sputtered onto the disc, covering the microscopic bumps. A thin layer of acrylic is then sprayed or spin-coated over the reflective layer to protect it and provide a surface for labeling. Pits are often referred to when discussing CDs instead of bumps. Pits appear on the reflective side, bumps appear on the side the laser reads from. An optical media player performs the task of finding and reading the data stored as bumps on the optical storage media substrate. In the case of DVDs, the injection-molded substrate impressed with a spiral track of data is half the thickness of a CD (nominally 0.6 mm). The substrate is sputtered with a reflective metal layer and then is bonded to another polycarbonate substrate (also nominally 0.6 mm) using a UV-curable adhesive.

For example, referring to FIG. 1, in various embodiments the optical storage media 10 of the present disclosure can include a plurality of layers, which includes a film or layer of sensor spots 70. These layers include, but are not limited to, a first substrate layer 20 made of a thermoplastic, such as a polycarbonate or the like; a second substrate layer 60 also made of a thermoplastic, such as a polycarbonate or the like; a reflective layer 40 made of a metal, such as aluminum, silver or gold, or the like; optionally, either a "data layer" which includes regions of pits and lands molded into the second substrate and/or a recording layer 50 made of a recordable material, such as phthalocyanine or the like, or a re-writable material, such as an MO material, a phase-change material, a chalcogenide or the like; a bonding adhesive layer 30; and a sensor spot layer or film 70 covering regions of the second substrate 60. Each of the layers is described in greater detail hereinbelow.

It should be noted that, although preferred layer combinations are illustrated and described herein, other layer combinations will be readily apparent to those of ordinary skill in the art and are contemplated by the present disclosure.

The plastic employed for both the first substrate 20 and second substrate 60 should be capable of withstanding subsequent processing parameters (e.g., application of subsequent layers) such as sputtering temperatures of about room temperature (about 25° C.) up to about 150° C., and subsequent storage conditions (e.g., in a hot car having temperatures up to about 70° C.). That is, it is desirable for the plastic to have sufficient thermal and mechanical stability to prevent deformation during the various layer deposition steps as well as during storage by the end-user. Possible plastics include thermoplastics with glass transition temperatures of about 100° C. or greater, with about 125° C. or greater preferred, about 140° C. or greater more preferred, and about 200° C. or greater even more preferred (e.g., polyetherimides, polyetheretherketones, polysulfones, polyethersulfones, polyetherethersulfones, polyphenylene ethers, polyimides, polycarbonates, etc.). Materials having glass transition temperatures greater than about 250° C. are most preferred, such as polyetherimide in which sulfonedianiline or oxydianiline has been substituted for m-phenylenediamine, among others, as well as polyimides, combinations comprising at least one of the foregoing plastics, and others. Generally, polycarbonates are employed.

Other examples of materials which may be used as first substrate 20 and second substrate 60 include, but are not limited to, amorphous, crystalline, and semi-crystalline thermoplastic materials such as: polyvinyl chloride, polyolefins (including, but not limited to, linear and cyclic polyolefins and including polyethylene, chlorinated polyethylene, polypropylene, and the like), polyesters (including, but not limited to, polyethylene terephthalate, polybutylene terephthalate, polycyclohexylmethylene terephthalate, and the like), polyamides, polysulfones (including, but not limited to, hydrogenated polysulfones, and the like), polyimides, polyether imides, polyether sulfones, polyphenylene sulfides, polyether ketones, polyether ether ketones, ABS resins, polystyrenes (including, but not limited to, hydrogenated polystyrenes, syndiotactic and atactic polystyrenes, polycyclohexyl ethylene, styrene-co-acrylonitrile, styrene-co-maleic anhydride, and the like), polybutadiene, polyacrylates (including, but not limited to, polymethylmethacrylate (PMMA), methyl methacrylate-polyimide copolymers, and the like), polyacrylonitrile, polyacetals, polycarbonates, polyphenylene ethers (including, but not limited to, those derived from 2,6-dimethylphenol and copolymers with 2,3,6-trimethylphenol, and the like), ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, and tetrafluoroethylenes (e.g., Teflons).

Optical storage media 10 of the present disclosure can be produced by first forming the substrate material using a conventional reaction vessel capable of adequately mixing various precursors, such as a single or twin-screw extruder, kneader, blender, or the like. The extruder should be maintained at a sufficiently high temperature to melt the substrate material precursors without causing decomposition thereof. For polycarbonate, for example, temperatures in a range between about 220° C. and about 360° C. can be used, and preferably in a range between about 260° C. and about 320° C. Similarly, the residence time in the extruder should be controlled to minimize decomposition. Residence times of up to about 2 minutes (min) or more can be employed, with up to about 1.5 min preferred, and up to about 1 min especially preferred. Prior to extrusion into the desired form (typically pellets, sheets, webs, or the like), the mixture can optionally be filtered, such as by melt filtering, the use of a screen pack, or combinations thereof, to remove undesirable contaminants or decomposition products.

Once the plastic composition has been produced, it can be formed into the substrate using various molding techniques, processing techniques, or combinations thereof. Possible techniques include injection molding, film casting, extrusion, press molding, blow molding, stamping, and the like. Once the substrate has been produced, additional processing, such as electroplating, coating techniques (e.g., spin coating, spray coating, vapor deposition, screen printing, painting, dipping, and the like), lamination, sputtering, and the like, as well as combinations comprising at least one of the foregoing processing techniques, may be employed to dispose desired layers on the substrate. Typically the substrate has a thickness of up to about 600 microns.

While not required, in some embodiments the optical storage media contains data encoded therein. In recordable media, the data are encoded by laser, which illuminates an active data layer that undergoes a phase change, thus producing a series of highly-reflecting or non-reflective regions making up the data stream. In these formats, a laser beam first travels through the substrate before reaching the data layer. At the data layer, the beam is either reflected or not, in accordance with the encoded data. The laser light then travels back through the substrate and into an optical detector system where the data are interpreted. Thus, the data layer is disposed between the substrate and the reflective layer. The data layer(s) for an optical application typically is pits, grooves, or combinations thereof on the substrate layer. Preferably, the data layer is embedded in the first substrate 20 surface. Typically, an injection molding-compression technique produces the substrate where a mold is filled with a molten polymer as defined herein. The mold may contain a preform, insert, etc. The polymer system is cooled and, while still in at least partially molten state, compressed to imprint the desired surface features, for example, pits and grooves, arranged in spiral concentric or other orientation onto the desired portions of the substrate, i.e., one or both sides in the desired areas.

Possible data layers for magnetic or magneto-optic applications may include any material capable of storing retrievable data and examples include, but are not limited to, oxides (such as silicone oxide), rare earth elements, transition metal alloys, nickel, cobalt, chromium, tantalum, platinum, terbium, gadolinium, iron, boron, others, and alloys and combinations comprising at least one of the foregoing, organic dyes (e.g., cyanine or phthalocyanine type dyes), and inorganic phase change compounds (e.g., TeSeSn, InAgSb, and the like).

Optionally, protective layer(s), which protect against dust, oils, and other contaminants, may be applied to the optical storage media of the present disclosure. These protective layers can have a thickness of greater than about 100 microns ($\mu$) to less than about 10 Angstroms (Å), with a thickness of about 300 Å or less preferred in some embodiments, and a thickness of about 100 Å or less especially preferred. The thickness of the protective layer(s) is usually determined, at least in part, by the type of read/write mechanism employed, e.g., magnetic, optic, or magneto-optic. Possible protective layers include anti-corrosive materials such as gold, silver, nitrides (e.g., silicon nitrides and aluminum nitrides, among others), carbides (e.g., silicon carbide and others), oxides (e.g., silicon dioxide and others), polymeric materials (e.g., polyacrylates or polycarbonates), carbon film (diamond, diamond-like carbon, and the like), among others, and combinations comprising at least one of the foregoing materials.

Dielectric layers may also be optionally included in the optical storage media of the present disclosure. Dielectric layer(s), where present, are typically disposed on one or both sides of the data layer and are often employed as heat controllers, and can typically have a thickness of up to or exceeding about 1,000 Å and as low as about 200 Å or less. Possible dielectric layers include nitrides (e.g., silicon nitride, aluminum nitride, and others); oxides (e.g., aluminum oxide); sulfides (e.g. zinc sulfide); carbides (e.g., silicon carbide); and combinations comprising at least one of the foregoing materials, among other materials compatible within the environment and preferably not reactive with the surrounding layers.

The reflective layer 40 should have a sufficient thickness to reflect a sufficient amount of energy (e.g., light) to enable data retrieval. Optionally, more than one reflective layer may be present. Typically the reflective layer(s) can have a thickness of up to about 700 Å or so, with a thickness in a range between about 300 Å and about 600 Å generally preferred. Possible reflective layers include any material capable of reflecting the particular energy field, including metals (e.g., aluminum, silver, gold, silicon, titanium, and alloys and mixtures comprising at least one of the foregoing metals, and others).

An adhesive layer 30 may also be present within optical storage media 10 which can adhere any combination of the above-mentioned layers. The adhesive layer can comprise any material that does not substantially interfere with the transfer of light through the media from and to the data retrieval device (e.g., that is substantially transparent at the wavelength of light utilized by the device, and/or which allows a reflectivity from the media of about 50% or greater, with a percent reflectivity of about 65% or greater preferred and a percent reflectivity of about 75% or greater more preferred). Possible adhesive materials include UV materials such as acrylates (e.g., cross-linked acrylates, and the like) silicone hardcoats, and the like, as well as reaction products and combinations comprising at least one of the foregoing materials. Other examples of UV materials are described in U.S. Pat. Nos. 4,179,548 and 4,491,508. Some useful monoacrylate monomers include butyl acrylate, hexyl acrylate, dodecyl acrylate and the like. Some useful polyfunctional acrylate monomers include, for example, diacrylates, triacrylates, tetraacrylates, and combinations thereof. Other adhesives which can be used in the adhesive layer include thermoplastic acrylic polymers, polyester resins, epoxy resins, polythiolenes, UV curable organic resins, pressure-sensitive adhesives, polyurethanes, thermosettable acrylic polymers, alkyds, vinyl resins, and reaction products and combinations comprising at least one of the foregoing adhesives.

Although the adhesive layer may contain only one of said polyfunctional acrylate monomers, or a mixture comprising at least one of the polyfunctional acrylate monomers (and the UV light reaction product thereof), preferred layers contain a mixture of two polyfunctional monomers (and the UV light reaction product thereof), preferably a diacrylate and a triacrylate (and the UV light reaction product thereof), with mono-acrylate monomers used in particular instances. Optionally, the adhesive layer can comprise nonacrylic UV curable aliphatically unsaturated organic monomers in amounts up to about 50 weight % of the uncured adhesive layer that includes, for example, such materials as N-vinyl pyrrolidone, styrene, and the like, and reaction products and combinations comprising at least one of the foregoing materials.

In other embodiments, an adhesive layer is not present in the optical storage media of the present disclosure.

The materials for the optical storage media substrate are not critical in type, and should preferably have a high light-transmittance. Examples of suitable materials include, but are not limited to, thermoplastic resins such as polycarbonates, polymethyl methacrylate and the like, and thermosetting resins such as epoxy resins, and the like. Of these, light-transmitting thermoplastic resins such as polycarbonates are preferred.

Methods for producing resins suitable for use as optical storage media substrates are known to those skilled in the art. In some cases, it is preferable to control the polymerization of the optical storage media substrate by endcapping. For example, upon polymerization of a polymer, a growing polymer chain has a reactive group at its end that is available for the continued growth of the polymer chain. When an alternative reaction occurs which results in the incorporation of a moiety without this reactive group, the ability of the chain to continue the chain extension is terminated. Chains with terminal groups of this type are said to be endcapped. In some embodiments, optical storage media are made from polycarbonate when diphenyl carbonate reacts with bisphenol A. In such a case, this reaction produces a growing polymer having a reactive hydroxyl group which is available for the continued growth of the polymer chain. When an alternative reaction occurs which results in the incorporation of a moiety without this reactive hydroxyl group, the ability of the chain to continue the chain extension is terminated or endcapped. A variety of endcapping reagents have been disclosed in the art, including those described in U.S. Pat. Nos. 4,774,315, 5,028,690, 5,043,203, 5,644,017 and 5,668,202.

Optionally, polycarbonate optical storage media can be made through a polycondensation process involving bisphenol monomers with phosgene or diphenyl carbonate and an optional monomer selected to alter the surface energy of the optionally treated and untreated optical storage media. Examples of surface energy modifying comonomers or additives include endcapping monomers such as monofunctional phenols, branching agents that result in increased endgroup formation, siloxane-containg monomers and additives, antistatic agents, antifogging agents, surface-segregating additives and other additives.

Once the optical storage media has been obtained, analyte-specific reagents are applied as sensor spots to the optical storage media article, such as a CD or DVD. As used herein, "sensor spots" and "sensor regions" are used interchangeably to describe sensor materials placed on the surface, or in an indentation placed in the surface but not penetrating the region containing the digital information, of an optical storage media at predetermined spatial locations for sensing using an optical storage media drive. Depending on the application, the sensor spots are responsive to physical, chemical, biochemical, and other changes in the environment.

Preferably, the analyte-specific reagent is attached to or incorporated into a sensor film, which is then applied to the optical media disc. Most preferably, the analyte-specific reagent on the sensor film forms sensor spots when applied to the optical storage media substrate. The polymers utilized in the sensor film are permeable to selected analytes where an analyte is a certain chemical species or class of chemical species detected by the sensor.

In one embodiment, an analyte-specific sensor element is immobilized within a polymer support or onto a preformed polymer support to form a sensor film. Preferably, the polymer support is compatible with the reagent. The polymer support of the sensor film is preferably a plastic film, i.e., a resin, of low concentration so as to not adversely affect the thickness of the optical storage media substrate and the optical properties of the article. The resin utilized to form the polymer support depends on the sensor applications. The resin may be dissolved in a solvent and the analyte-specific reagent may become dispersed in the liquid medium. Alternatively, the analyte-specific reagent may be applied directly to an already formed plastic film.

The polymeric material used to produce the sensor film may affect the detection properties such as selectivity, sensitivity, and limit of detection. Thus, suitable materials for the sensor film are selected from polymeric and/or inorganic materials capable of providing a desired response time, a desired permeability, desired solubility, degree of transparency and hardness, and other similar characteristics relevant to the material of interest to be analyzed. In some embodiments the film-forming polymeric support also includes inorganic materials.

Suitable polymer supports include conducting polymers such as poly(anilines), poly(thiophenes), poly(pyrroles), poly (acetylenes), etc.; main-chain carbon polymers such as poly (dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), etc.; main-chain acyclic heteroatom polymers such as poly (oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), etc.; and, main-chain heterocyclic polymers such as poly(benzoxazoles), poly(oxadiazoles), poly(benzothiazinophenothiazines), poly(benzothiazoles), poly(pyrazinoquinoxalines), poly(pyromellitimides), poly (quinoxalines), poly(benzimidazoles), poly(oxindoles), poly (oxoisoindolines), poly(dioxoisoindolines), poly(triazines), poly(pyridazines), poly(piperazines), poly(pyridines), poly (piperidines), poly(triazoles), poly(pyrazoles), poly(pyrrolidines), poly(carboranes), poly(oxabicyclononanes), poly (dibenzofurans), poly(phthalides), poly(acetals), poly (anhydrides), carbohydrates, etc. The polymer supports can be homopolymers, copolymers of monomeric constituents of the above-mentioned polymers or resins, or polymer blends of the foregoing resins produced using methods known to those skilled in the art.

Preferably, thermoplastic polymers may be used as the polymer support including, for example, resins such as poly (2-hydroxyethyl methacrylate), polystyrene, poly($\alpha$-methylstyrene), polyindene, poly(4-methyl-1-pentene), polyvinylpyridine, polyvinylformal, polyvinylacetal, polyvinylbutyral, polyvinyl acetate, polyvinyl alcohol, polyvinyl chloride, polyvinylidene chloride, polyvinyl methyl ether, polyvinyl ethyl ether, polyvinyl benzyl ether, polyvinyl methyl ketone, poly(N-vinylcarbazole), poly(N-vinylpyrrolidone), polymethyl acrylate, polyethyl acrylate, polyacrylic acid, polyacrylonitrile, polymethyl methacrylate, polyethyl methacrylate, polybutyl methacrylate, polybenzyl methacrylate, polycyclohexyl methacrylate, polymethacrylic acid, polyamide methacrylate, polymethacrylonitrile, polyacetaldehyde, polychloral, polyethylene oxide, polypropylene oxide, polyethylene terephthalate, polybutylene terephthalate, polycarbonates of bisphenols and carbonic acids, poly(diethylene glycol/bis-allylcarbonates), 6-nylon, 6,6-nylon, 12-nylon, 6,12-nylon, polyethyl asparatate, polyethyl glutamate, polylysine, polyproline, poly(γ-benzyl-L-glutamate), methyl cellulose, hydroxypropyl cellulose, acetyl cellulose, cellulose triacetate, cellulose tributylate, polyurethane resins and the like, organopolysiloxanes such as poly(phenylmethylsilane), organopolygermanium compounds, and copolymers or co-polycondensates of monomeric constituents in the above-mentioned polymers or resins. In addition, blends of the foregoing polymers may be utilized.

Other types of polymers which may be used as polymer supports in accordance with the present disclosure are hydrogels. A hydrogel is a three dimensional network of hydrophilic polymers which have been tied together to form water-swellable but water insoluble structures. The term hydrogel is to be applied to hydrophilic polymers in a dry state (xerogel) as well as in a wet state as described in U.S. Pat. No. 5,744,794. Where hydrogels are used, a number of different methods may be used to tie these hydrogels together. First, tying of hydrogels via radiation or free radical cross-linking of hydrophilic polymers may be utilized, examples being poly(acrylic acids), poly(methacrylic acids), poly(hydroxyethylmethacrylates), poly(glyceryl methacrylate), poly(vinyl alcohols), poly(ethylene oxides), poly(acrylamides), poly(N-acrylamides), poly(N,N-dimethylaminopropyl-N'-acrylamide), poly(ethylene imines), sodium/potassium poly(acrylates), polysaccharides, e.g. xanthates, alginates, guar gum, agarose etc., poly(vinyl pyrrolidone) and cellulose based derivatives. Second, tying via chemical cross-linking of hydrophilic polymers and monomers with appropriate polyfunctional monomers may be utilized, examples including poly(hydroxyethylmethacrylate) cross-linked with suitable agents such as N,N'-methylenebisacrylamide, polyethylene glycol diacrylate, triethylene glycol diacrylate, tetraethylene glycol dimethacrylate, tripropylene glycol diacrylate, pentaerythritol tetraacrylate, di-trimethylolpropane tetraacrylate, dipentaerythritol pentaacrylate, trimethylolpropane triacrylate, pentaerythritol triacrylate, propoxylated glyceryl triacrylate, ethoxylated pentaerythritol tetraacrylate, ethoxylated trimethylolpropane triacrylate, hexanediol diacrylate, hexanediol dimethacrylate and other di- and tri-acrylates and methacrylates; the copolymerisation of hydroxyethylmethacrylate monomer with dimethacrylate ester crosslinking agents; poly(ethylene oxide) based polyurethanes prepared through the reaction of hydroxyl-terminated poly(ethylene glycols) with polyisocyanates or by the reaction with diisocyanates in the presence of polyfunctional monomers such as triols; and cellulose derivates cross-linked with dialdehydes, diepoxides and polybasic acids. Third, tying via incorporation of hydrophilic monomers and polymers into block and graft copolymers, examples being block and graft copolymers of poly(ethylene oxide) with suitable polymers such as poly(ethyleneglycol) (PEG), acrylic acid (AA), poly(vinyl pyrrolidone), poly(vinyl acetate), poly(vinyl alcohol), N,N-dimethylaminoethyl methacrylate, poly(acrylamide-co-methyl methacrylate), poly(N-isopropylacrylamide), poly(hydroxypropyl methacrylate-co-N,N-dimethylaminoethyl methacrylate); poly(vinyl pyrrolidone)-co-polystyrene copolymers; poly(vinyl pyrrolidone)-co-vinyl alcohol copolymers; polyurethanes; polyurethaneureas; polyurethaneureas based on poly(ethylene oxide); polyurethaneureas and poly(acrylonitrile)-co-poly(acrylic acid) copolymers; and a variety of derivatives of poly(acrylonitriles), poly(vinyl alcohols) and poly(acrylic acids). Molecular complex formation may also occur between hydrophilic polymers and other polymers, examples being poly(ethylene oxides) hydrogel complexes with poly(acrylic acids) and poly(methacrylic acids). Last, tying via entanglement cross-linking of high molecular weight hydrophilic polymers, examples being hydrogels based on high molecular weight poly(ethylene oxides) admixed with polyfunctional acrylic or vinyl monomers. As noted above, copolymers or co-polycondensates of monomeric constituents of the above-mentioned polymers, and blends of the foregoing polymers, may also be utilized.

Examples of applications of these materials are in Michie, et al., "Distributed pH and water detection using fiber-optic sensors and hydrogels," J. Lightwave Technol. 1995, 13, 1415-1420; Bownass, et al., "Serially multiplexed point sensor for the detection of high humidity in passive optical networks," Opt. Lett. 1997, 22, 346-348; and U.S. Pat. No. 5,744,794.

The resin making up the polymer support may be dissolved in a suitable solvent including, but not limited to, 1-methoxy-2-propanol, ethanol, acetone, chloroform, toluene, xylene, benzene, isopropyl alcohol, 2-ethoxyethanol, 2-butoxyethanol, methylene chloride, tetrahydrofuran, ethylene glycol diacetate. Generally, the concentration of the solvent in the solution containing the resin is about 70 weight percent or greater, with about 75 weight percent or greater preferred.

In other embodiments, an amorphous fluoropolymer can be dissolved in perfluoro(2-butyl tetrahydrofuran) and a thin film from polymer solution can be deposited onto the surface of the disc. Films made of amorphous fluoropolymers are extremely stable upon exposure even to nonpolar solvents that completely dissolve conventional polymeric films with immobilized reagents. Thus, highly robust sensor spots and sensor arrays can be built using these materials where an amorphous fluoropolymer film is deposited on top or under a sensor film, or both, to protect the sensor film from degradation.

In other embodiments, a nonpolymer sensor film can be can be deposited onto the surface of the disc. An example of such a nonpolymer film is a metal film that changes its reflectivity and/or transmission as a function of environment.

The polymer support of the sensor film is preferably permeable to selected analytes. The sensor film may be selectively permeable to analytes on the basis of size, i.e., molecular weight; hydrophobic/hydrophilic properties; phase, i.e., whether the analyte is a liquid, gas or solid; solubility; ion charge; or the ability to inhibit diffusion of colloidal or particulate material.

The permeability of a polymer support is provided by a physical variation of the polymer properties such as free volume, porosity, orientation of the polymer chains. Chemically-selective polymers, which are used in some embodiments, are polymers that can preferentially transport certain analytes. Examples of chemically-selective polymers include silicone polymers that transport nonionic analytes and do not appreciably transport ionic analytes.

In other embodiments, size-selective polymers may be used. Size-selective polymers are polymers that can preferentially transport certain analytes as a function of their molecular size and molecular weight. An example includes cellulose nitrate, cellulose acetate, and magna-R polymers that transport analytes as a function of their molecular size and molecular weight.

Where hydrogels are used as the polymer support, selective permeability can be based on size exclusion (i.e., molecular weight or the inhibition of diffusion of colloidal or particulate material). Similarly, Teflon AF can be utilized to allow selective diffusion of small nonionic species over ionic species, and copolymers can be designed with selective hydrophobic/hydrophilic diffusion preferences. (See, e.g., U.S. Pat. No. 6,500,547 and U.S. Patent Publication No. 2002/0173040).

More detailed examples of polymers are described by Freud, et al., "A chemically diverse conducting polymer-based 'electronic nose'", Proc. Natl. Acad. Sci. USA 1995, 92, 2652-2656; Albert, et al., "Cross-reactive chemical sensor arrays," Chem. Rev. 2000, 1000, 2595-2626; Grate, et al. "Handbook of Biosensors and Electronic Noses. Medicine, Food, and the Environment"; E. Kress-Rogers, Ed.; CRC Press: Boca Raton, FL, 1997; pp 593-612; Grate, et al., "Solubility interactions and the design of chemically selective sorbent coatings for chemical sensors and arrays," Sens. Actuators B 1991, 3, 85-111; U.S. Pat. Nos. 6,010,616 and 6,093,308.

Other polymer supports which may be utilized include copolymers, polymer blends, and physical mixtures of the above polymers with additives such as organic and inorganic pigments; conducting, semiconducting, and non-conducting particles; inorganic sol-gel materials produced by condensation reactions, which can be doped with organic components; and polyelectrolytes, such as high-density polyethylene grafted with poly(styrenesulfonic acid), perfluorosulfonate ionomers including those sold as Nafion® by DuPont, and others.

Once the appropriate polymer support has been selected, chemically sensitive reagents, i.e., analyte-specific reagents, are incorporated into, or applied to, the polymer support to produce the sensor film. Materials utilized as analyte-specific reagents incorporate dyes and reagents known in the art as sensor materials. As used herein, "analyte-specific reagents" are compounds that exhibit calorimetric, photorefractive, photochromic, thermochromic, fluorescent, elastic scattering, inelastic scattering, polarization, and any other optical property useful for detecting physical, chemical and biological species. Analyte-specific reagents include organic and inorganic dyes and pigments, nanocrystals, nanoparticles, quantum dots, organic fluorophores, inorganic fluorophores and similar materials.

Examples of organic compounds which can be used as analyte-specific reagents include organic dyes, organic fluorophores, fluorescent dyes, IR absorbing dyes, UV absorbing dyes, photochromic dyes, thermochromic dyes, and other known dyes that may be used for this purpose. Specific examples of dyes include xanthene dyes such as rhodamine B, rhodamine 6G, eosine, phloxine B and the like, acridine dyes such as acridine orange, acridine red and the like, azo dyes such as ethyl red, methyl red and the like, porphyrin dyes, phthalocyanine dyes, cyanine dyes such as 3,3'-diethylthiacarbocyanine iodide, 3,3'-diethyloxadicarbocyanine iodide and the like, merocyanine dyes, styryl dyes, oxonol dyes, triarylmethane dyes, methylene blue, phenol blue and the like. Other dyes including pH sensitive dyes such as bromothymol blue and bromocresol green may similarly be used. These dyes may be used singly or in combination depending on the desired application. The choice of organic compound and amount utilized for a given application depends on the properties of the organic compound and the purpose for which it will be used. For instance, fluorescent dyes may be added to a resin binder on the order of ppm as is known in the art.

Fluorescent materials which may be used as analyte-specific reagents bond to specific predetermined locations on the sensor film and fluoresce when excited by a specific optical wavelength. Appropriate wavelengths range from about 200 nm to about 1100 nm, more preferably from about 300 nm to about 1000 nm, with a range of from about 350 nm to about 950 nm being most preferred. Nonlimiting examples of these materials are presented in Table 1.

TABLE 1

Examples of materials for fluorescent sensors

| Analyte-specific reagent material | Excitation wavelength (nm) | Emission wavelength (nm) |
|---|---|---|
| Tris(di(4-bromo)-benzoylmethane)-mono(phenanthroline)europium (III) | ~400 | ~615 |
| Tris(dibiphenoylmethane)-mono(phenanthroline)europium (III) | ~410 | ~615 |
| Tris(2-phenylpyridine)iridium (III) | ~400 | ~515 |
| Cresyl violet | ~600 | ~630 |
| Nile blue | ~633 | ~675 |
| Oxazine 1 | ~645 | ~670 |
| Oxazine 4 | ~615 | ~660 |
| Rhodamine 700 | ~645 | ~700 |
| DDI | ~710 | ~745 |
| IR125 | ~795 | ~840 |
| DTTCI | ~760 | ~815 |
| HDITCI | ~780 | ~825 |
| CdSe nanoparticles, crystal diameter = 2.8 nm | ~520 | ~535 |
| CdSe nanoparticles, crystal diameter = 3.4 nm | ~545 | ~560 |
| CdSe nanoparticles, crystal diameter = 4.0 nm | ~575 | ~585 |
| CdSe nanoparticles, crystal diameter = 4.7 nm | ~595 | ~610 |
| CdSe nanoparticles, crystal diameter = 5.6 nm | ~625 | ~640 |

In other embodiments, non-fluorescing analyte-specific reagents that bond to specific predetermined locations may be used. Such reagents include light absorbing materials such as near infrared (NIR) absorbing materials. Examples of NIR absorbing materials include carbon black and Poly(styrenesulfonate)/poly(2,3-dihydrothieno(3,4-b)-1,4-dioxin).

In one embodiment, the analyte-specific reagent is a light absorbing reagent absorbing light at about 650 nm. In another embodiment, the analyte-specific reagent is a light absorbing reagent absorbing light at about 780 nm. In another embodiment, the analyte-specific reagent is a light absorbing reagent absorbing light at about 405 nm. Nonlimiting examples of other suitable light absorbing materials which may be utilized as analyte-specific reagents and appropriate wavelengths for detection are presented in Table 2.

TABLE 2

Examples of materials for non-fluorescent sensors

| Analyte-specific reagent material | Absorption wavelength (nm) |
|---|---|
| Photochromic quinones | 400-800 |
| Photochromic viologens | 400-800 |
| Spirooxazines | 400-750 |
| Spiropyrans | 400-750 |

Other materials which may be used as analyte-specific reagents include thermochromic compounds. Examples of thermochromic compounds include several dyes available from Matsui-color. They also include IR absorbing compounds such as phthalocyanine dyes, cobalt or platinum complexes/chelates, some VAT dyes such as anthraquinone and methylene blue, nigrosine compounds such as Keystone Black R or Anirox, and conjugated polymers/oligomers especially in the doped form (polyaniline, polyphenylenes, polythiophenes, polypyrroles and their derivatives).

Heat-absorbing compounds may also be used as analyte-specific reagents. Examples of heat-absorbing compounds include microencapsulated sprayable liquid crystals, including room temperature liquid crystals. They are available, for example, from Liquid Crystal Resources, Inc., with a wide range of transition temperatures. An example of a room temperature liquid crystal is SPC/R25C5W from Liquid Crystal Resources, Inc.

Additionally, temperature sensitive scattering compounds may be utilized in accordance with the present disclosure. Examples of temperature sensitive scattering compounds include salts in a matrix just above the critical concentration at room temperature, and polymer blends that are below the lower critical solution temperature (LCST) at room temperature.

Materials that undergo a change in their refractive index may also be used as the analyte specific reagent. Examples of materials with refractive index changes include liquid crystal polymers, polymers developed for holographic data storage where their refractive index or birefringence changes when temperature increases.

As noted above, the analyte-specific reagents also include nanocrystals, nanoparticles and quantum dots and are known to those skilled in the art. Suitable nanocrystals include, but are not limited to, those made of $MoS_2$, ZnO, Si, CdTe, and Ge. Suitable nanoparticles include, but are not limited to, those made of Cu, $SiO_2$, and $LaB_6$. Quantum dots, as used herein, include, but are not limited to, those made of PbS, CdSe, and PbSe.

As noted above, analyte-specific reagents can be incorporated into the polymeric support during synthesis or separately applied to a pre-formed polymer support. The resulting sensor film may be coated onto the surface of the optical storage media substrate using any of a number of techniques including painting, spraying, spin-coating, dipping, screen-printing and the like. For example, in one embodiment, the polymer support and analyte-specific reagent are dissolved in a relatively volatile organic solvent, said solvent being substantially inert towards the optical data storage disc (meaning that the solvent will not attack or otherwise adversely affect the optical data storage disc), and the solution of the sensor film is applied directly to the surface of the optical storage media substrate. Generally, the concentration of the plastic sensor film in the solvent is greater than about 1 weight percent and less than about 25 weight percent, and preferably greater than about 10 weight percent and less than about 20 weight percent.

In some cases, the sensor film applied to the optical storage media substrate may be subjected to treatment to form discrete sensor areas, i.e., sensor spots. Methods for such application are known to those skilled in the art and include physical masking systems and both negative and positive photoresist applications.

In general, physical masking systems are utilized to modify unmasked regions of the surface of the optical storage media. The mask comprises one or more holes disposed therethrough or openings disposed therein. Each of the one or more holes or openings may be, for example, substantially circular, oblong, square, rectangular, triangular or a more complex shape. The mask is disposed adjacent to a surface of the optical storage media such that light passing through each of the plurality of holes is selectively prevented or shielded from contacting predetermined locations of the surface of the optical storage media. A shutter may be disposed above the mask. The shutter is a mechanical device that selectively allows/prevents light from contacting the surface of the optical storage media by opening/closing. In one example, a mask having openings ranging from about 1 mm to about 10 mm may be applied onto the surface of the optical storage media. Light, e.g. UV light, may then be applied through the mask to catalyze a reaction resulting in the creation of sensor spots of desired size and shape. The modified regions may differ in thickness and shape across the surface of the article. Typically, the mask comprises a plate, sheet, film, coating or the like.

In a negative resist embodiment, the analyte-specific reagent can be a light sensitive dye such as methylene blue that is dispersed within the sensor film. If the film is irradiated with light through a photomask, the dye molecules that are irradiated are destroyed or otherwise converted to a state that renders them ineffective as a sensor. The remaining active dye forms the sensor spot.

In a positive resist embodiment, the analyte-specific reagent is dispersed in the coating in an inactive form, for example, containing a photolabile moiety. Upon irradiation with light, the reagent is converted into the active form necessary for operation of the sensor. The size and shape of the sensor would again be determined by the light that is allowed to propagate through a photomask. Other examples of positive and negative photoresist chemistry and methodology are known and include those disclosed in the following references: Tetrahedron Letters, No. 12, pp 1029-1030, 1979; Proc. Natl. Acad. Sci. USA, Vol 96, pp 1193-1200, February 1999; Tetrahedron Letters, 40, pp 1441-1444, 1999; Synthesis, pp 1-15, January 1980; U.S. Pat. No. 6,472,541 and US Patent Application Publication Nos. 20030186427 and 20030144499. It is contemplated that any of the photolabile protecting groups disclosed in the above mentioned references may be useful as precursors or reagents in sensor applications. Other protection groups are known in the art that may be removed by means other than through the use of light. One example described in U.S. Pat. No. 5,625,081 is a protected fluorescent dye wherein acyloxy protecting groups are removed by use of aqueous ammonia.

In other embodiments, analyte specific reagents are applied to pre-formed polymer supports. In these cases, the analyte-specific reagents can be applied to pre-formed polymeric supports by methods known to those skilled in the art including, but not limited to, ink-jet printing, microarraying, robotic spotting, screen printing, etc. In a subsequent step, the film with the analyte-specific reagent is illuminated with light in combination with a physical masking system in order to catalyze a reaction resulting in the creation of sensor spots of desired size and shapes.

In some cases, an adhesive may be applied to the surface of an optical storage media substrate followed by the application of the sensor film to the adhesive to enhance adherence of the sensor film to the optical storage media substrate. Adhesives suitable for such applications are preferably transparent and known to those skilled in the art. One example of a suitable adhesive is a CD lacquer such as Daicure 2200 from DIC. Other suitable adhesives which may be used to bind the sensor film to the optical storage media include those described above as suitable for use as adhesive layer 30 in an optical storage media 10 (as depicted in FIG. 1.) The coating of adhesive can be applied by methods known to those skilled in the art, including painting, spraying, spin-coating, dipping, screen-printing and the like. In one case, the adhesive is spin-coated onto the data side of an optical storage media substrate such as a DVD.

Pressure sensitive adhesives may be used in some embodiments. The optical storage media substrate and sensor film are contacted by applying a pressure sensitive adhesive to one surface of the sensor film, and then bringing the optical storage media substrate into contact under positive pressure with the pressure sensitive adhesive. The pressure-sensitive adhesive may be water-based such as acrylic, vinyl acrylic, styrene acrylic, urethane acrylic, butyl acrylate and other acrylic emulsions or cross-linked alkyl acrylic esters, rubber-based adhesives such as those based on styrene-butadiene-styrene copolymers, epoxides, silicone-based adhesives such as blends of silicone resin with polydiorganosiloxane. Water-based acrylic polymer emulsion pressure sensitive adhesive suitable for use according to the method of the present disclosure include Gelva GME 2234 from Solutia, 72.9292 from National Starch & Chemical Co., and Phoplex N-500 from Rohm & Haas Co. Solvent-based pressure sensitive adhesives suitable for use according to the method of the present disclosure include Gelva GMS 1753 from Solutia, and Durotak 80-1058 from National Starch & Chemical, and mixtures thereof. Water-based and solvent-based liquid pressure sensitive adhesives can be applied to a moving web of plastic protective film using standard coating methods including Meyer rod, gravure, knife over-roll, and 3 and 4-roll reverse roll coating to form an adhesive-coated plastic sensor film. Typically, the pressure sensitive adhesive-coated plastic sensor film is then dried, cut into an appropriate size and shape, and then contacted with the surface of the optical storage media substrate. The resulting sandwich structure comprising the plastic sensor film, pressure sensitive adhesive and the optical storage media substrate may then be passed through a laminator to ensure good adhesion of the plastic sensor film to the optical storage media substrate.

In one embodiment the pressure sensitive adhesive-coated plastic sensor film is laminated to a silicone coated backer to protect the pressure sensitive adhesive. In application, the backer can be removed to expose the pressure sensitive adhesive which is then utilized to apply the sensor film to the optical storage media substrate. These pressure sensitive adhesives may also be used as adhesive layer 30 of an optical storage media 10 as depicted in FIG. 1.

In one embodiment the adhesive layer is cured after pieces of the sensor film are applied to the optical storage media substrate. The coated optical storage media substrate is typically illuminated with a UV light source to cure the adhesive. The adhesive may also be cured with heat, reaction with air and/or water, or removal of a reaction byproduct. Examples of suitable UV light sources include a Xenon Corp. RC747 pulsed UV/Vis system with a spiral lamp. Curing times upon exposure to the UV light source at a light energy of about 0.5 J/cm$^2$ can vary from about 0.5 seconds to about 10 seconds, with a range of from about 1 second to about 5 seconds being preferred. In one embodiment, the time for cure is about 2 seconds. The resulting film/optical storage media substrate structure is clear and of good quality with good adhesion between the sensor film and optical storage media substrate. Additional light sources may also be used for this purpose. A partial list is given below in Table 3.

TABLE 3

Light sources for curing of adhesives.

| Source | Spectral range of emission (nm) |
|---|---|
| Continuous wave sources: | |
| Xenon arc lamp | 200-1000 |
| Mercury arc lamp | 250-600 |
| Deuterium lamp | 180-420 |
| Tungsten lamp | 320-2500 |
| Light emitting diodes | different diodes cover range from 370 to 1500 nm |
| Diode lasers | different diode lasers cover range from about 400 to 1500 nm |
| Argon ion laser | several lines over 350-514 nm |
| Pulsed sources: | |
| Nitrogen laser | 337 nm |
| Nd:YAG laser | frequency tripled - 355; frequency quadrupled - 266 |
| Dye lasers | frequency doubled 200-450 |

As noted above, the sensor films of the present disclosure can be applied to the entire surface of the optical storage media article and thereafter treated so the resulting sensor contains the analyte-specific reagents in discrete locations, i.e., sensor spots. In other embodiments, the sensor films of the present disclosure may be placed onto a predetermined region of an optical storage media substrate. The use of the sensor film thus permits the mass production of sensor spots, which may be placed on selected regions of the disc before exposure to a fluid of interest.

The sensor film may also optionally contain various additives such as flattening agents, surface active agents, thixotropic agents, and the like, and reaction products and combinations comprising at least one of the foregoing additives. Materials of the optical storage media can be selected and/or modified to provide required properties for the retention of the analyte-specific reagent and film on the surface of the optical storage media substrate. These modifications may include, but are not limited to, the use of different copolymer materials, additives, endcapping and any other modifications known in the art.

In other embodiments, a sensor film of the present disclosure may also be applied to a second transparent plastic film, which is then applied to an optical storage media article. Such a second transparent plastic film may have its own adhesive layer attached to one side of the film. The structure of sensor film on a transparent film can be exposed to an analyte before or after application of the sensor film to the optical storage media substrate.

In some cases, a sensor film can be attached to a transparent film, which is then attached to an optical storage media substrate. In this case the sensor film is on top of the transparent film and is exposed to the environment; the transparent film, in turn, is between the optical storage media substrate and the sensor film. In this embodiment, the sensor spot can be periodically exposed to the environment and readings can be obtained in time to follow the kinetics of a reaction.

In another embodiment, the sensor film attached to the transparent film may be applied to an optical storage media substrate such that the sensor film is between the transparent film and the optical storage media substrate. In this embodiment, the sensor spot can be exposed to the environment once and then protected by having the transparent film exposed to the environment.

Examples of transparent plastic films with adhesive layers which may be used in the above embodiments include commercially available tapes such as those sold by Lovett Brand as scotch tape. The film is attached to a DVD or CD and uniformly distributed pressure is applied to the film. The resulting film/DVD structure is clear and of good quality.

In other embodiments, preformed transparent plastic circular films may be used, including CD anti-scratch protective films such as d-skin from d-skin LLC or Model CLR-33, and can be placed onto a whole disc. Other suitable films are commercially available from Quieve Technologies, Inc. The film can be attached to an optical storage media substrate with an adhesive as described above. Once the film has been applied, a sensor region containing an analyte-specific reagent can be applied onto the transparent circular film. The sensor film can be applied to the transparent plastic film before application to the optical disk. In this way, the transparent plastic film with sensor regions can be exposed to a sample of interest and then can be applied onto the optical disk for analysis.

In other embodiments, deposition of the sensor film is performed preferably without any intermediate layers such as adhesives. Such deposition is accomplished by wetting a surface of the optical storage media substrate with a relevant solvent (for example, 1-methoxy-2-propanol, isopropyl alcohol, ethyl alcohol, ethanol, and/or 2-propanol) followed by deposition of a region of a sensor film containing a reagent. An example of the film is a poly(2-hydroxyethyl methacrylate) film with a pH reagent such as bromothymol blue or bromocresol green. The films can be formed by dissolving poly(2-hydroxyethyl methacrylate) polymer in 1-methoxy-2-propanol at a suitable polymer concentration. The pH reagent is added and films can then be produced by coating the polymer solution onto a flat inert optical storage media substrate such as an optical storage media. So, for example, poly(2-hydroxyethyl methacrylate) polymer in 1-methoxy-2-propanol at an appropriate polymer concentration can be spin coated over the sensor spots to secure them to the disk. Alternatively, the surface of the disk could be wet with a suitable solvent such as 1-methoxy-2-propanol prior to placement of the sensor spots to promote adhesion.

In another embodiment, multiple sensor spots cut out from preformed films as described above are adhered to an optical media by simple electrostatic adhesion with uniform external pressure. In some cases the sensor spots thus adhered to the media by pressure and electrostatic adhesion are immobilized in their position further by controlled thermal annealing. The portions on the optical media with the sensor spots are selectively exposed to infra-red radiation to raise the temperature of the spots to one above the glass transition temperature (Tg) of the polymer matrix, but below the Tg of polycarbonate, and subsequently cooled to ambient temperature.

In yet another embodiment, crosslinking reagents could be used to cross-react the sensor film with the support media, e.g. UV-activated cross linkers might be used. In this embodiment, a reagent is immobilized into the polymer matrix base of the sensor film from a reagent solution in a solvent.

The adhesion of sensor spots with the discs can further be improved in most of the above deposition techniques by surface pretreatment of the discs with controlled UV exposure, chemical surface pretreatment or post deposition annealing at an elevated temperature, or annealing in a solvent-rich atmosphere.

Once obtained, discs possessing sensor spots in accordance with the present disclosure may be exposed to a sample for detection of an analyte of interest. For example, where a pH sensitive reagent such as bromothymol blue or bromocresol green is used, the sensor spot can be exposed to vapor or liquids which may include ammonia and the sensor read to confirm the presence of and the amounts of such an alkaline vapor. Such a film may be placed on an optical storage media substrate and then exposed to an analyte, or such a film may be exposed to a sample containing an analyte and then placed on a optical storage media substrate.

To reduce the problem of the degradation of sensor spot integrity upon contact with environmental contaminants, pollutants, solvents, etc., in one embodiment of the present disclosure an additional thin solvent-resistant overlayer is applied over the sensor spot. Such an overlayer protects the sensor spot from degradation. An overlayer can contain different additives that promote the improvement in selectivity of chemical determinations. The overlayer itself can function as a selective membrane to species that are passing through the overlayer to the sensing layer.

Suitable solvent-resistant overlayers are permeable to analytes, whether in liquid or gas form, but are impermeable and resistant to environmental contaminants, pollutants, and solvents. Thus, the solvent-resistant overlayer functions as a selective membrane permitting permeation of the analyte in question but preventing entry of contaminants into the sensor. As noted above, the overlayer can be a separate transparent film. In some cases, the solvent-resistive overlayer can be uniformly applied over the entire disk and utilized to hold the sensor spots in position.

In other embodiments, the sensor film is exposed to a fluid of interest, and the protective overlayer is applied over the sensor spots to reduce the environmental effects and/or increase the recovery time of the sensor spot and to allow the measurements of the sensor spots in the optical storage media drive. In such a case the sensor film can be exposed to the fluid of interest either before or after application to the optical storage media substrate.

In one embodiment, the solvent-resistant overlayer is a random copolymer of tetrafluoroethylene (TFE) and perfluoro-2,2-dimethyl-1,3-dioxole (PDD) sold under the trademark Teflon® AF; for a discussion of the uses of Teflon® AF, see Lowry, et al., "Optical Characteristics of Teflon AF Fluoroplastic Materials", Opt. Eng. 1992, 31, pp. 1982-1985). Other solvent-resistant overlayers include perfluorosulfonate ionomers sold under the trademark Nafion® and hydrogels such as poly(hydroxyethylmethacrylates) which are not dissolved by water. Other suitable hydrogels which may be used as the solvent-resistant overlayer include those possessing selective permeability properties as described above as suitable materials for use as the polymer support of the sensor film.

In one embodiment, an analyte-specific reagent is immobilized onto a transparent film to form a sensor spot. In this embodiment, the sensor film with at least one sensor spot is exposed to a sample, such as a fluid or vapor, and subsequent to exposure the sensor film is then attached to an optical storage media for reading in an optical storage media drive.

After exposure to a sample, a readout of the analyte-specific reagent may be performed inside the optical storage media drive. The optical drive can detect changes in the physical and chemical properties of the sensor spots. The sensor device is placed in an optical storage media drive, which is capable of analyzing the properties of the analyte-specific reagent to determine the presence or absence of the analyte. Preferably, a readout of the optical storage media containing the analyte-specific reagent may be performed using lasers employed in optical storage media drives in the conventional reading of optical storage media substrates.

Information provided from the optical storage media is of both chemical/biological and non-chemical/non-biological nature. A sensor spot can provide an average signal that minimizes test-to-test variations. An array of spots can provide an average signal that minimizes test-to-test variations.

In one embodiment, each sensor spot covers multiple pit/land areas. This feature of the sensor region provides the ability to average signals across different regions of the same sensor spot to improve the signal-to-noise ratio. The term "covers" refers to the spot being located between the laser incident surface of the optical storage media substrate and the data layer containing pits and lands. The spot can be located in a coating layer not necessarily adjacent to the pit/land layer, but rather in the optical path of the laser to a specific pit/land region.

An array of sensor spots containing chemical reagents at different concentrations that react to completion with a corresponding concentration of a certain analyte could also be used. The array of sensor spots contains different chemical reagents that respond to physical and chemical properties of the analyte and environment. In some cases the array of sensor spots contain chemical reagents that are catalyzed and begin to react upon stimulus (i.e., light) from the optical drive.

Detection can also be performed over time from the same sensor spot to provide information about reaction kinetics.

In another embodiment, an array of sensor spots detects nonchemical parameters of the environment. Nonlimiting examples of these parameters include physical, mechanical, dielectric, electric, magnetic, and other non-chemical parameters. More specific examples are temperature, viscosity, pressure, oxidation-reduction potential, permeability, molecular weight, porosity, hydrophobicity, surface energy, solution conductivity, etc.

Where a fluorophore is used as the analyte-specific reagent, the excitation wavelengths of the fluorophores are in the range of operation of a variety of available light sources and of laser diodes used in conventional readers/recorders of optical media. In one embodiment, a readout (excitation) of the analyte-specific reagents may be performed using the laser diodes. In an alternative embodiment, the reading of the analyte-specific reagents is done outside of the optical storage media drive. Although one embodiment of an optical media reader which may be used to read a disc with a sensor film is discussed below, it is to be understood that the methods of the present disclosure may be employed using any optical media reader known in the art.

Conventional optical readers which may be used to read a disc with a sensor film contain optical read/write pick-up mechanisms attached to a tracking mechanism. Typically, both the optical read/write head and the tracking mechanism are positioned adjacent to the surface of a spinning optical storage media substrate during operation. The optical read/write head includes a light source, such as a laser diode or the like, operable for transmitting encoded/un-encoded light, such as laser light or the like, to the surface of the optical storage media substrate. The optical read/write head also includes a light receiving device, such as a photodiode or the like, operable for receiving encoded/un-encoded light, such as laser light or the like, from the surface of the optical storage media substrate. A reflective element, such as a semi-reflective mirror, a beam splitter, or the like, and a focusing lens or other focusing optics may also be used to transmit the light to and/or receive the light from the surface of the optical storage media substrate.

Using the optical read/write head, analyte-specific reagents and data can be read from predetermined portions of the surface of the optical storage media substrate via the selective positioning of the tracking mechanism and the optical read/write head. Typically, the tracking mechanism includes a pick-up carrier assembly movably attached to one or more guide rails, a portion of which may be threaded. In conjunction with a servo motor or the like, the one or more guide rails are operable for moving the tracking mechanism and the optical read/write head linearly with respect to the surface of the optical storage media substrate. Readings can be performed from the sensor spots after exposure to environmental sample without a measurement step of sensor spots before the exposure to environmental sample. Alternatively, once the baseline readings for an optical storage media article with sensor spots has been obtained, the sensor spots may be exposed to a sample, such as an environmental sample, for determination of the presence of a specific analyte. In those cases where the analyte is present and reacts with the analyte-specific reagent, the reaction with the analyte-specific reagent alters either the light transmittance, scatter, polarization, optical path length, or a combination of these parameters, from the optical storage media article thereby providing a signal which demonstrates the presence of the analyte in question. Sensor spots with the same chemical composition and dedicated for measurements of the same environmental parameter can be exposed to the environmental parameter for different amounts of time to obtain an improved quantitation in measurements where at least one sensor spot is not exposed to the environmental parameter and serves as for the baseline reading.

In the embodiments where the sensor spot is placed onto the film, the spot can be first exposed to the sample, and then placed onto a disc for reading. The presence of an analyte in question is determined from the response of the sensor spot from the available response curve of similar sensor spots to the analyte in question.

In addition, as noted above, the sensor film can have more than one sensor spots. Sensor spots with the same chemical composition and dedicated for measurements of the same environmental parameter can be exposed to the environmental parameter for different amounts of time to obtain an improved quantitation in measurements where at least one sensor spot is not exposed to the environmental parameter and serves as for the baseline reading.

While the above disclosure has been directed to the application of the sensor films of the present disclosure to an optical storage media article which are read in optical readers, in other embodiments the sensor films may be applied to other substrates and read using other methods. Suitable substrates include any plastic or glass substrate with a geometry that matches the layout of the sensor spots. The substrate provides support for the sensor film or transparent film. Examples of useful geometries include a disk geometry, a square geometry, and a strip geometry. In such a case, the sensor region on the sensor film can be exposed to a sample of interest and then can be analyzed by any available reflection or transmission detector. Nonlimiting examples of such detectors include a UV-visible spectrometer (such as Hewlett Packard Model 8452A (a diode array spectrometer)) handheld photometers and spectrophotometers such as Ocean Optics Model USB2000, Hach Model DR-2010, Hach Model 890, Merck Reflectoquant, and other similar detectors known to those skilled in the art. In such a case, a substrate other than an optical storage media substrate may be utilized.

The present disclosure will now be described more specifically with reference to the following examples. It is to be noted that the following examples are presented herein for purpose of illustration and description; they are not intended to be exhaustive or to limit the disclosure to the precise form disclosed.

EXAMPLE 1

A reagent film was immobilized onto a preformed film to allow test spots to be produced in mass and then placed on selective regions of the disc before exposure to a fluid of interest.

Figure 2:
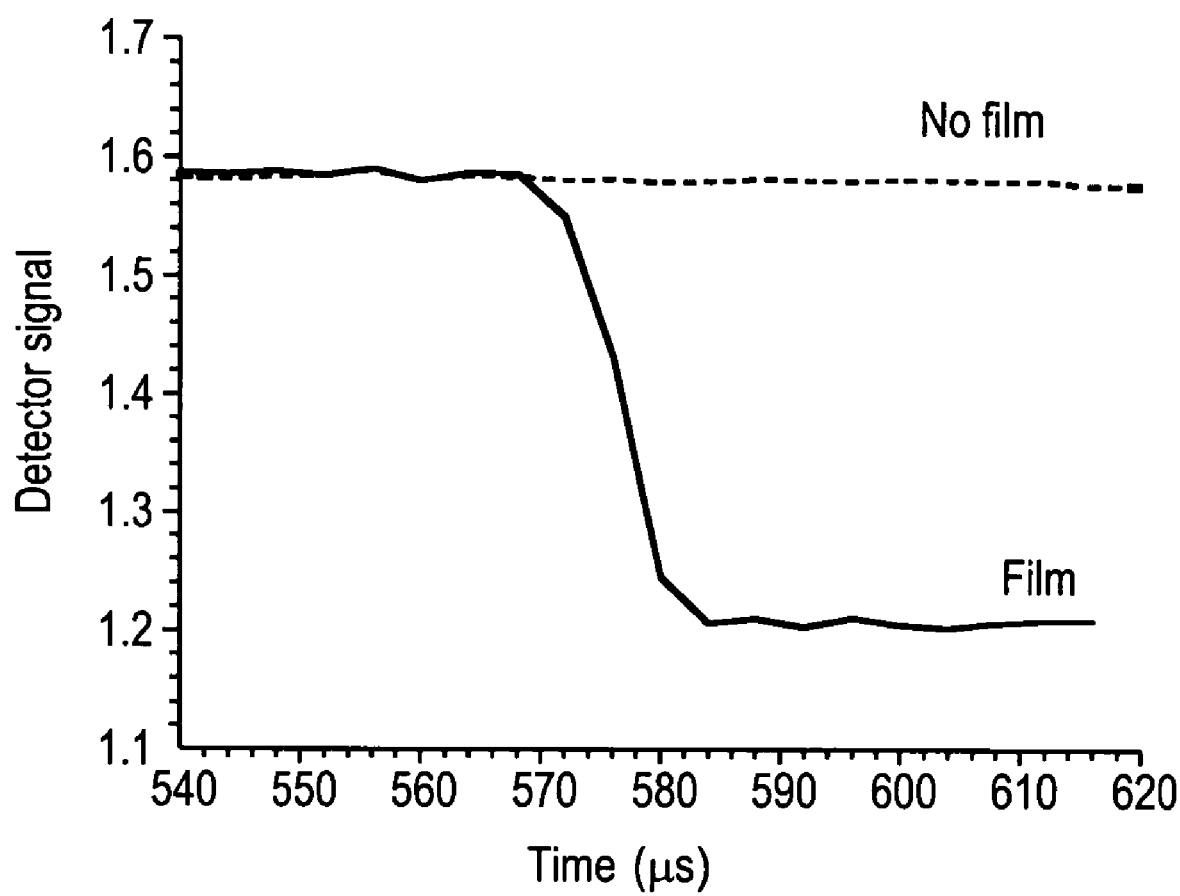
FIG. 2 is a graph depicting the results of screening a DVD coated in accordance with the present disclosure in an optical drive.

The transparent plastic film utilized had a pressure-sensitive-adhesive layer attached to one side of the film (3M 9483 optically clear adhesive film, 10 mil.). The film was attached to the DVD and uniformly distributed pressure was applied to the film. The resulting film/DVD structure was clear and of good quality. The DVD was screened in an optical drive and results of the analysis are shown in FIG. 2 demonstrating the signal produced from regions of the DVD with and without the coated film. As can be seen in FIG. 2, the clear film produced a large signal change upon analysis of DVD with the film. This large signal change precluded this film to be used as a support for DVD sensor.

A second disc was then prepared. An adhesive layer was first applied to the DVD. The adhesive utilized was the CD lacquer Daicure 2200 commercially available from DIC. The coating of Daicure 2200 was spin-coated onto the data side of a DVD. Pieces of reagent film were then applied to the lacquer. The coated DVD was then illuminated with UV using a Xenon Corp. RC747 flash lamp for 2 sec to cure the lacquer. The resulting film/DVD structure was clear and of good quality with good adhesion between the reagent film and DVD.

Figure 3:
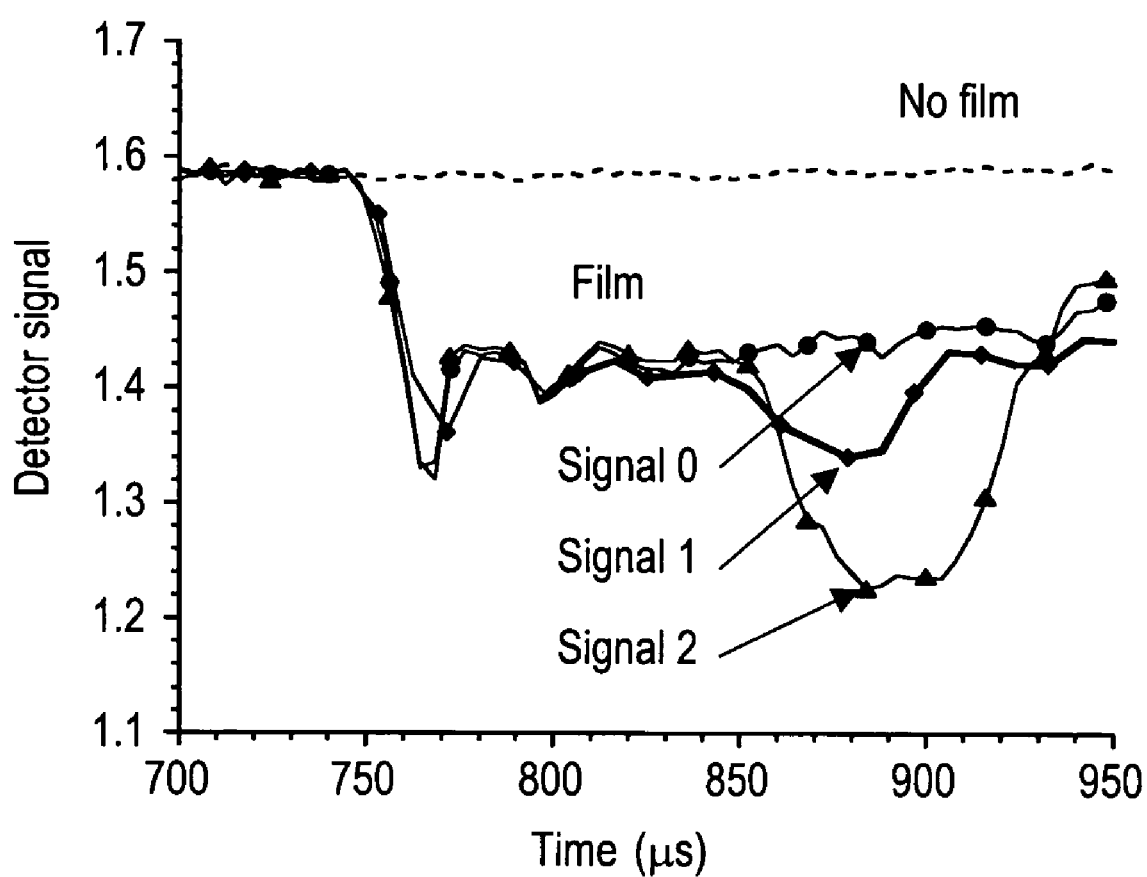
FIG. 3 is a graph depicting the results of screening a DVD coated in accordance with the present disclosure in an optical drive.

An additional film layer was formed as follows: A transparent plastic film was selected with an adhesive layer attached to one side of the film (Lovett Brand scotch tape). An appropriately sized reagent film was attached to a DVD and uniformly distributed pressure was applied to the film. The resulting film/DVD structure was clear and of good quality. The DVD was screened in an optical drive and results of the analysis are shown in FIG. 3 where the signal was produced from regions of the DVD with and without the coated film. The film produced only a small signal change upon analysis of DVD with the film. Thus, this film was suitable for use with analyte-sensitive materials in accordance with the present disclosure.

The clear film attached to the disc with an adhesive layer was then modified by applying a low level of absorbing material, in this case carbon black, dispersed in an alcohol-based solvent. The absorbing material was applied as a 1-mm wide line through the center of the film using a draw-coating method. After the measurement was done, the absorbing material was reapplied as a 1-mm wide line at approximately twice the loading of the absorbing material over the existing low-absorbing line. FIG. 3 shows increasing levels of the signal change from a region of the film modified with the absorbing material at different absorbing levels. The signal levels 0, 1, and 2 correspond to no absorbance from the film (signal 0) and increasing absorbance values (signals 1 and 2).

EXAMPLE 2

Figure 4B:
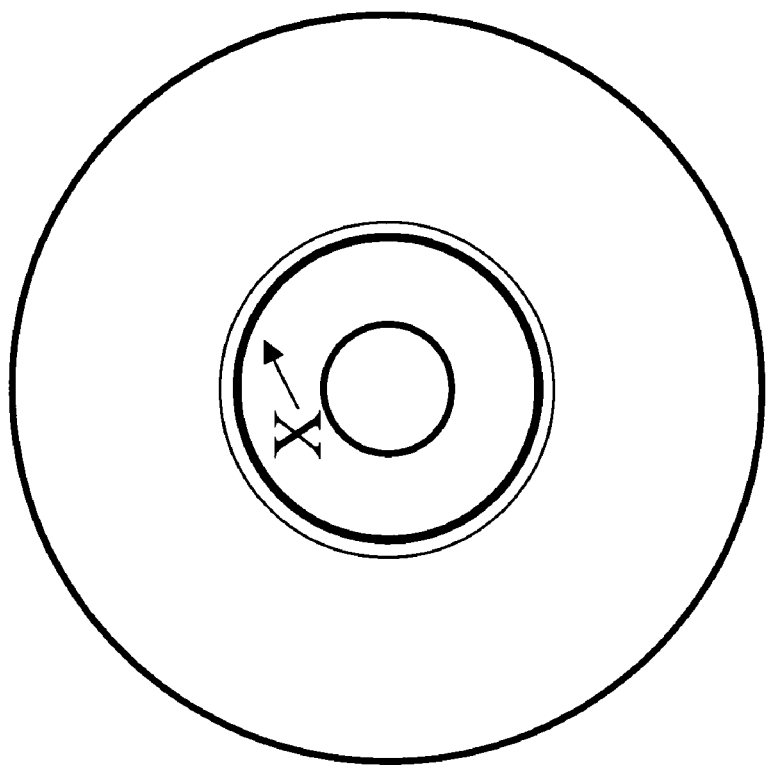
FIG. 4(B) is the optical storage media after application of the film.
Figure 4A:
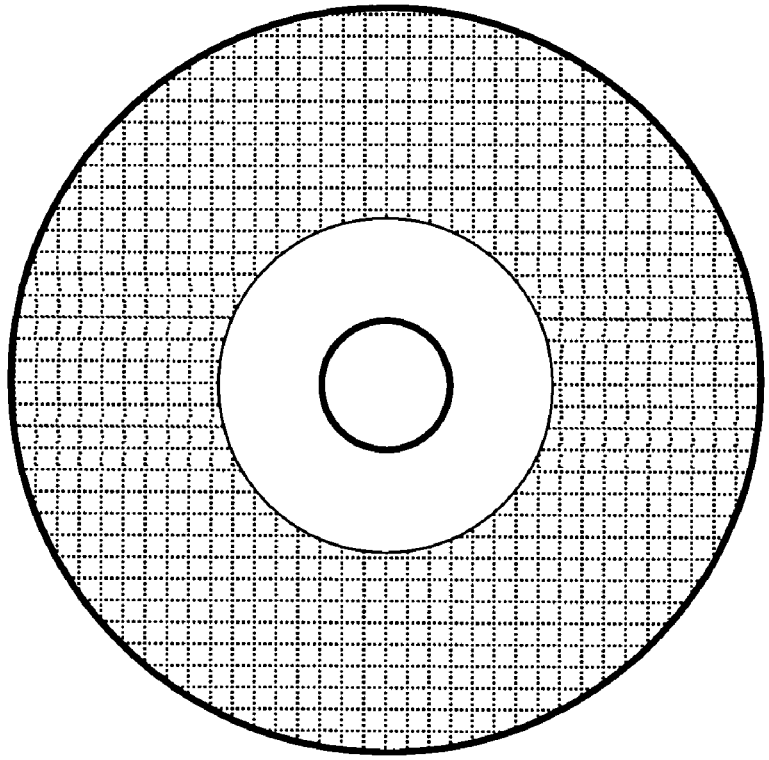
FIG. 4(A) is the optical storage media before application of the film.

Carbon black dispersed in an alcohol-based solvent was immobilized onto an optical disk at decreasing concentrations to allow test spots to have different absorbance levels. The level of absorbance of the absorbing film was provided by the amount of carbon black pigment per spot on the optical disk. The optical disk was screened in an optical drive (Pioneer DVD Drive, Model 115). A preformed transparent plastic circular film (CD Protective Film Model CLR-33), as depicted in FIG. 4A, was placed onto a whole disc. The film was attached at the inner edge of the film with an adhesive provided with the film (CD Protective Film Model CLR-33) as depicted as "X" in FIG. 4B.

Figure 5:
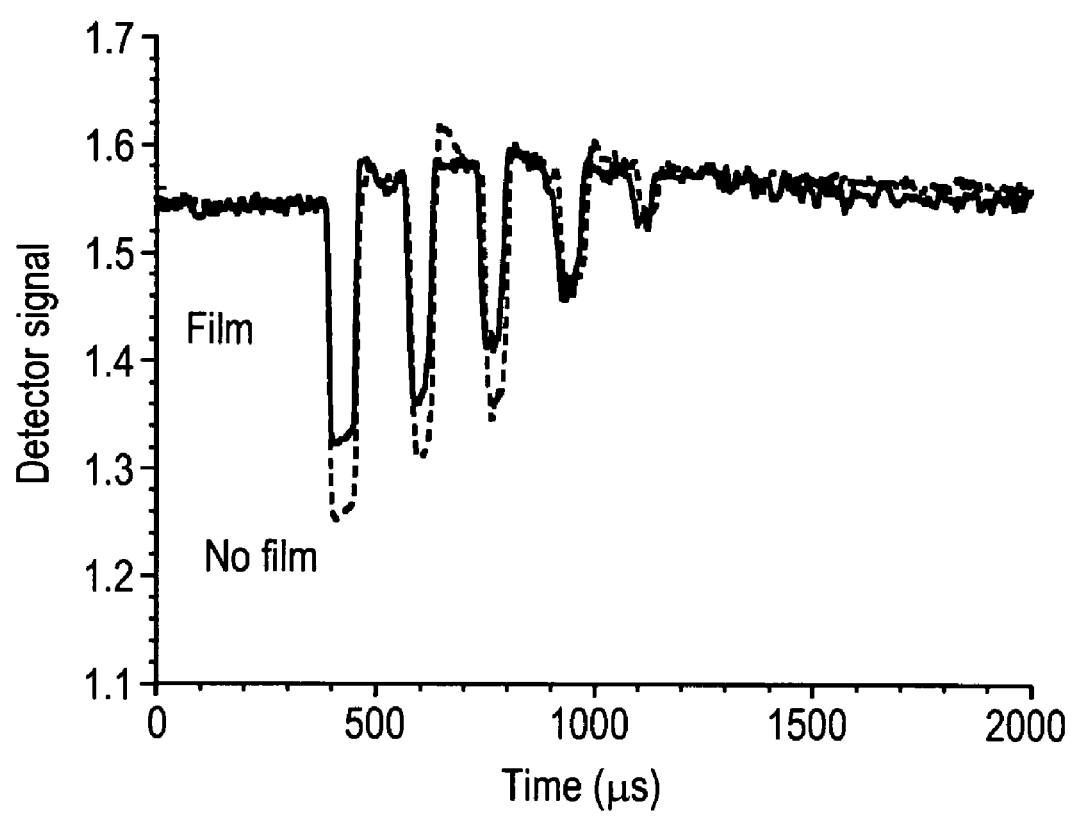
FIG. 5 is a graph depicting the results of absorbance measurements of regions of a disc with and without the attached overlayer film.
Figure 6:
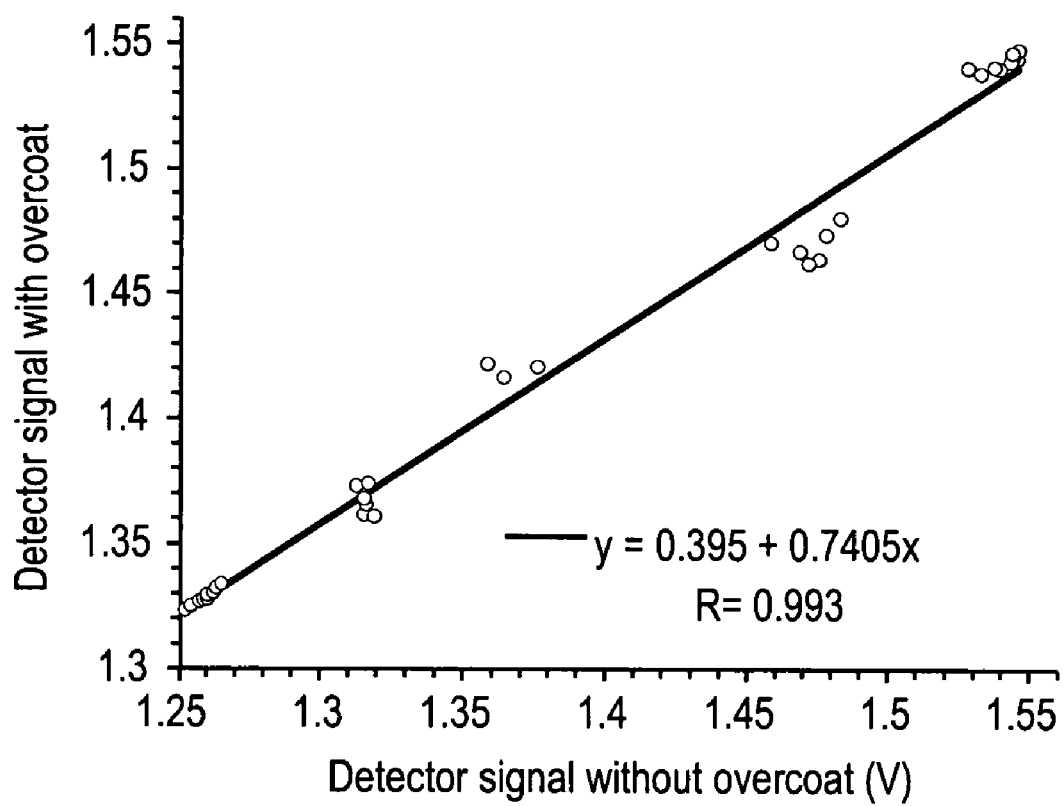
FIG. 6 is a graphical depiction of the correlation between absorbance-related CD signals measured with and without the overcoat film.

The resulting film/optical storage media structure was clear and of good quality. The CD was screened again with the film on top on the absorbing regions and results of the analysis are shown in FIG. 5 where the signal was obtained from regions of increasing absorbance on the optical disk both with and without the attached film. Correlation between absorbance-related optical disk signals obtained for regions both having and lacking the overcoat film is demonstrated in FIG. 6.

Figure 7:
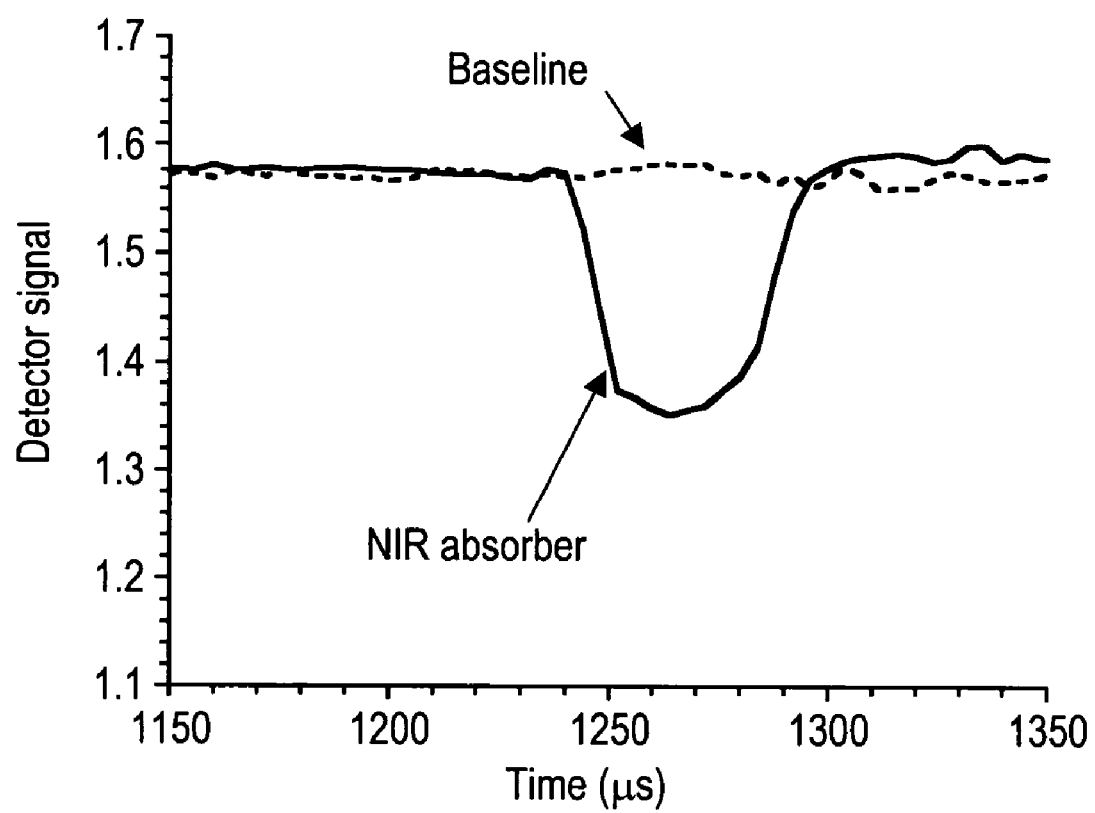
FIG. 7 is a graph depicting the signal obtained from the overcoat film without a sensor region (baseline) and with an absorbing sensor region (an NIR absorber).

Next, a light-absorbing region comprising a finely dispersed carbon black was applied onto the overcoat film. Carbon black was dispersed in an alcohol-based solvent and was applied onto the preformed transparent film using a draw-coating method. Signals were obtained in the optical drive as above. Examples of the signals obtained from the overcoat film without an absorbing region (baseline) and with an absorbing region (with carbon black as an NIR absorber) are presented in FIG. 7. As can be seen in FIG. 7, the overcoat film did not produce an appreciable signal attenuation and thus was suitable as a support for the deposition of sensor films.

Figure 8:
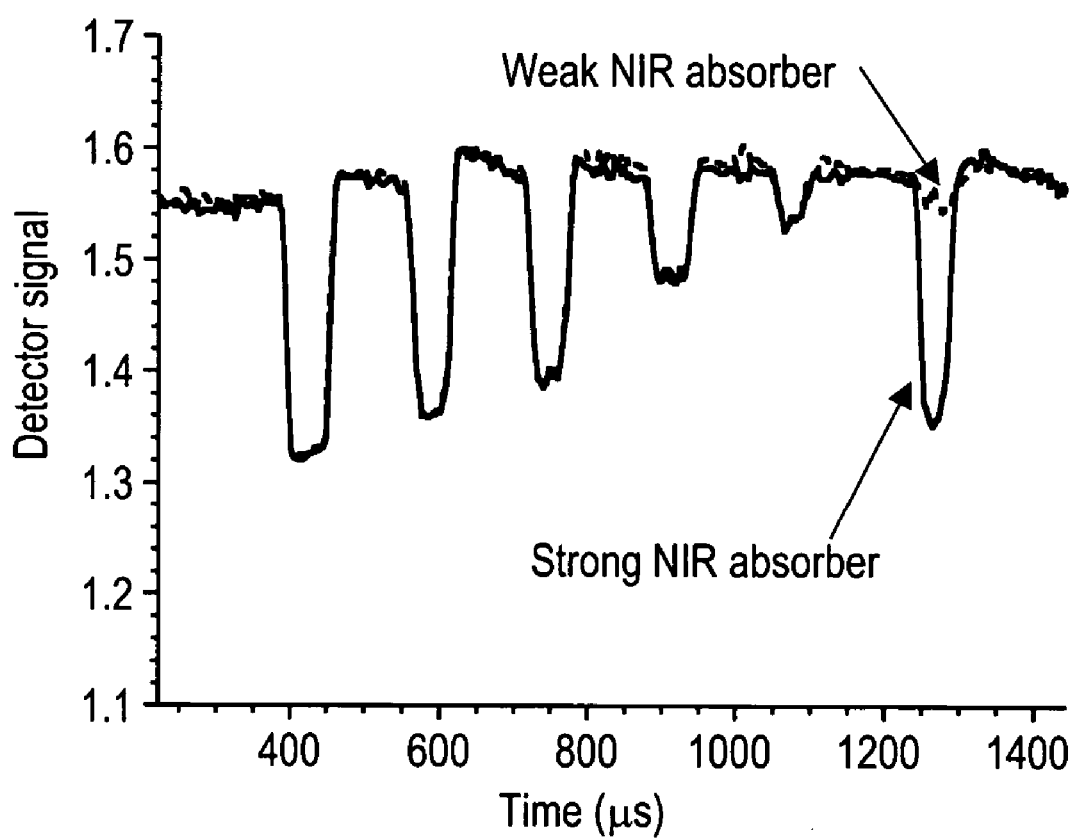
FIG. 8 is a graph depicting the signal obtained from the overcoat film with NIR absorber sensor regions having both weak and strong absorbing regions.

Two levels of absorbing materials were the applied onto the overcoat film to generate different levels of measured absorbance. FIG. 8 illustrates signals from the overcoat film with sensor regions that contain low and highly absorbing regions of NIR absorbers.

EXAMPLE 3

A pH reagent, bromocresol green, was immobilized by mechanical immobilization into a poly(2-hydroxyethyl methacrylate) film to allow test spots to be produced in mass and then placed on selective regions of the disc before exposure to ammonia vapor. Thus, each film possessed a poly(2-hydroxyethyl methacrylate) polymer support with the reagent incorporated into this support. The film was formed by dissolving poly(2-hydroxyethyl methacrylate) polymer in 1-methoxy-2-propanol at an appropriate polymer concentration. After immobilization of the sensor reagent, the film was placed onto a predetermined region of the disc.

Films were produced by draw-coating the polymer solution onto a flat inert optical storage media substrate. The dried films were peeled-off from the optical storage media substrate and precut to the sizes of interest (about 3×4 mm). The film was deposited without any intermediate layers such as adhesives onto the disc by wetting the surface of the disc with 1-methoxy-2-propanol followed by deposition of the film onto the optical storage media substrate by applying pressure.

Figure 9:
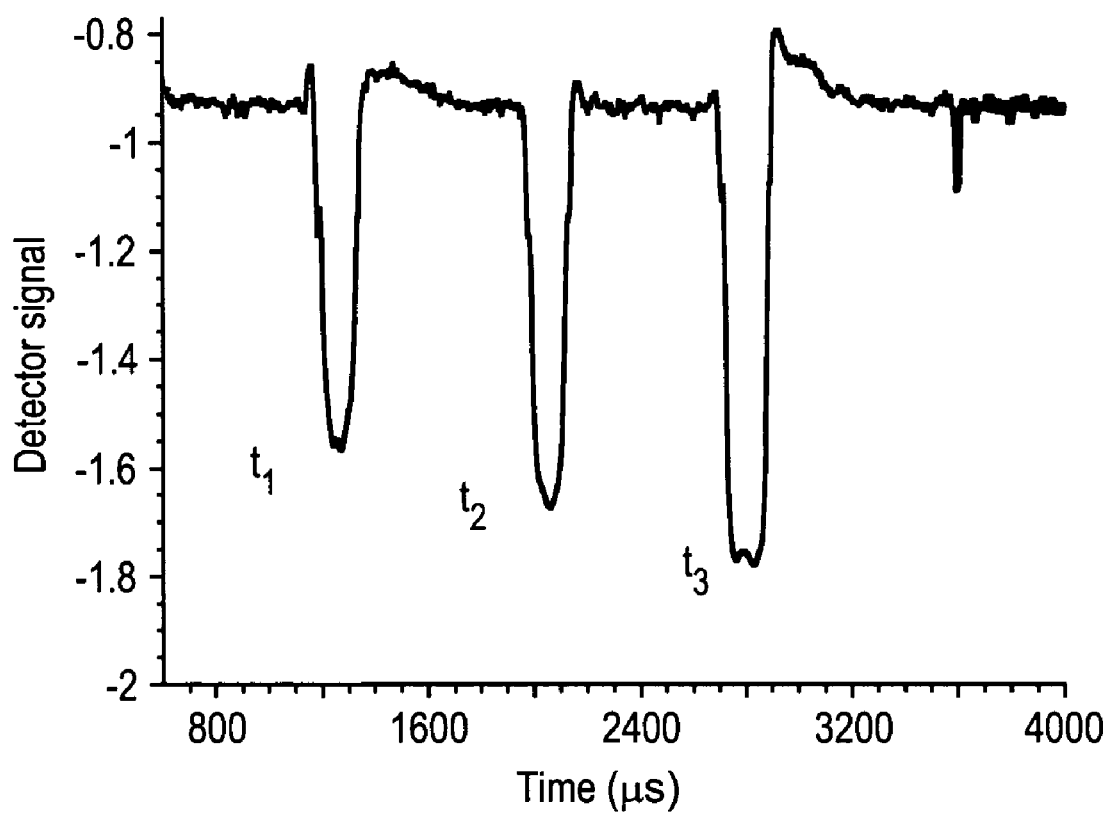
FIG. 9 is a graph depicting the response of three sensor regions as recorded using an optical drive. Different sensor regions were exposed to saturated ammonia vapor for different amounts of time (t1<t2<t3).

Several films with an acid-base reagent, bromocresol green, were attached onto a DVD optical storage media. The films were exposed at different exposure times to an alkaline vapor (ammonia) at a saturation vapor concentration at room temperature and normal atmospheric pressure. The different levels of these exposures were provided by varying the exposure times from 0 to about 20 seconds. FIG. 9 shows the response of three sensor regions as recorded using an optical drive (LG Electronics, Inc., Model GCC4480B) where different sensor regions were exposed to saturated ammonia vapor for different amounts of time ($t_1 < t_2 < t_3$).

EXAMPLE 4

Figure 10:
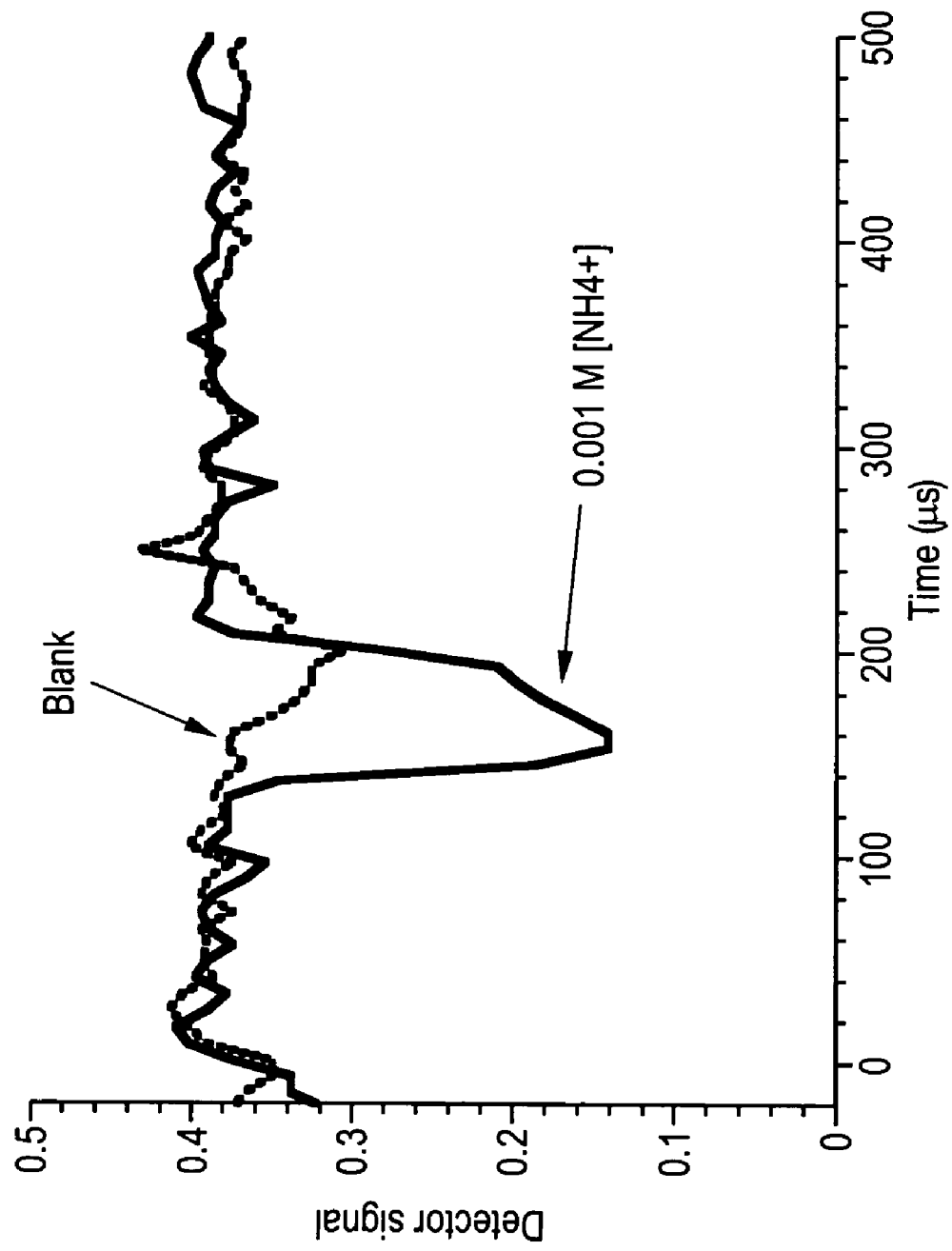
FIG. 10 is a graph illustrating changes in an optical signal of a sensor spot for detection of $NH_4^+$.

For detection of ionic species in water such as $NH_4^+$, thin film regions containing different pH dyes were produced on the DVD surface. These dyes included bromocresol green (Aldrich, 11,435-9), bromophenol blue (Nutritional Biochemicals, 12-238), and bromocresol purple (Aldrich, 86,089-1, 90% dye content). The dyes were dissolved in Nafion polymer solution purchased from Aldrich. The dye-Nafion solutions were deposited onto DVDs. After solvent evaporation at room temperature, the films were coated with an overcoat. The overcoat was a Teflon AF 2400 film. The overcoat film composition was produced by dissolving Teflon AF 2400 (from DuPont) in Fluorinert 75 solvent (from 3M). The initial signal of the films was measured followed by the exposure of the disk to an 0.001 moles per liter $NH_4^+$ solution. Upon removal from the solution, the disk was measured again. The change in sensor signal of the sensor films before and after exposure to $NH_4^+$ were observed as shown in FIG. 10. The signal change observed was associated with the color change from yellow to blue and respective absorbance increase at the wavelength of the DVD laser.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

The invention claimed is:

1. A sensor device comprising:
an optical storage medium; and
a sensor film comprising a polymer support in combination with ananalyte-specific reagent applied to at least a portion of the optical storage medium, wherein the polymer support is selected from the group consisting of poly(anilines), poly(thiophenes), poly(acetylenes), poly(alkenes), poly(dienes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), poly(benzoxazoles), poly(oxadiazoles), poly(benzothiazinophenothiazines), poly(benzothiazoles), poly(pyrazinoquinoxalines), poly(pyromellitimides), poly(quinoxalines), poly(benizimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), and copolymers of monomeric constituents of the above;
said polymer support comprising a hydrogel wherein the hydrogel is tied via radical cross-linking of hydrophilic polymers selected from the group consisting of poly(acrylic acids), poly(methacrylic acids), poly(hydroxyethylmethacrylates), poly(glyceryl methacrylates), poly(vinyl alcohols), poly(ethylene oxides), poly(acrylamides), poly(N-acrylamides), poly(N,N-dimethylaminopropyl-N'-acrylamides), poly(ethylene imines), sodium poly(acrylates), potassium poly(acrylates) polysaccharides, poly(vinyl pyrrolidones), cellulose derivatives, and copolymers of monomeric constituents of the above.

2. The sensor device of claim 1 wherein the hydrogel is a poly(hydroxyethylmethacrylate) hydrogel tied via chemical cross-linking with an agent selected from the group consisting of N,N'-methylenebisacrylamide, polyethylene glycol diacrylate, triethylene glycol diacrylate, tetraethylene glycol dimethacrylate, tripropylene glycol diacrylate, pentaerythritol tetraacrylate, di-trimethylolpropane tetraacrylate, dipentaerythritol pentaacrylate, trimethylolpropane triacrylate, pentaerythritol triacrylate, propoxylated glyceryl triacrylate, ethoxylated pentaerythritol tetraacrylate, ethoxylated trimethylolpropane triacrylate, hexanediol diacrylate, and hexanediol dimethacrylate.

3. The sensor device of claim 1 wherein the hydrogel is a cellulose derivative tied via chemical cross-linking with an agent selected from the group consisting of dialdehydes, diepoxides, and polybasic acids.

4. The sensor device of claim 1 wherein the hydrogel is a graft copolymer of poly(ethylene oxide) with polymers selected from the group consisting of poly(ethyleneglycol), poly(acrylic acid), poly(vinyl pyrrolidone), poly(vinyl acetate), poly(vinyl alcohol), N,N-dimethylaminoethyl methacrylate, poly(acrylamide-co-methyl methacrylate), poly(N-isopropylacrylamide), and poly(hydroxypropyl methacrylate-co-N,N-dimethylaminoethyl methacrylate).

5. The sensor device of claim 1 wherein the hydrogel is a graft copolymer selected from the group consisting of poly(vinyl pyrrolidone)-co-polystyrene copolymers, polyurethanes, polyurethaneureas in combination with poly(ethylene oxide), polynrethaneureas in combination with poly(acrylonitrile)-co-poly(acrylic acid), poly(acrylonitrile) derivatives, poly(vinyl alcohol) derivatives, and poly(acrylic acid) derivatives.

6. The sensor device of claim 1 wherein the polymer support comprises a polymer blend.

7. The sensor device of claim 1 wherein the sensor film is selectively permeable to an analyte on the basis of size of the analyte.

8. The sensor device of claim 1 wherein the sensor film is selectively permeable to an analyte on the basis of phase of the analyte.

9. The sensor device of claim 1 wherein the sensor film is selectively permeable to an analyte on the basis of solubility of the analyte.

10. The sensor device of claim 1 wherein the sensor film is selectively permeable to an analyte on the basis of ion charge of the analyte.

11. The sensor device of claim 1 wherein the analyte-specific reagent is selected from the group consisting of organic dyes, inorganic dyes, nanocrystals, nanoparticles, quantum dots, organic fluorophores, inorganic fluorophores, IR absorbing dyes, near infrared absorbing materials, UV absorbing dyes, photochromic dyes, and thermochromic dyes.

12. The sensor device of claim 1 wherein the analyte-specific reagent is selected from the group consisting of xanthene dyes, acridine dyes, azo dyes, porphyrin dyes, phthalocyanine dyes, cyanine dyes, merocyanine dyes, styryl dyes, oxonol dyes, triarylmethane dyes, methylene blue, phenol blue, bromothymol blue and bromocresol green.

13. The sensor device of claim 1 wherein the analyte-specific reagent is a light absorbing reagent selected from the group consisting of carbon black, photochromic quinones, photochromic viologens, spirooxazines, and spiropyrans.

14. The sensor device of claim 1 wherein the analyte-specific reagent is responsive to light at about 200 nm to about 1100 nm.

15. The sensor device of claim 1 wherein the analyte-specific reagent is responsive to light at about 300 nm to about 1000 nm.

16. The sensor device of claim 1 wherein the analyte-specific reagent is responsive to light at about 350 nm to about 950 nm.

17. The sensor device of claim 1 further comprising an adhesive to adhere the sensor film to the optical storage medium.

18. The sensor device of claim 17 wherein the adhesive comprises a pressure sensitive adhesive.

19. The sensor device of claim 1 further comprising a solvent-resistant overlayer over the sensor film.

20. The sensor device of claim 19 wherein the solvent-resistant overlayer is selected from the group consisting of random copolymers of tetrafluoroethylene and perfluoro-2,2-dimethyl-1,3-dioxole, perfluorosulfonate ionomers, and hydrogels.

* * * * *

UNITED STATES PATENT AND TRADEMARK OFFICE
CERTIFICATE OF CORRECTION

PATENT NO.       : 7,524,455 B2                                    Page 1 of 1
APPLICATION NO.  : 10/723536
DATED            : April 28, 2009
INVENTOR(S)      : Potyrailo et al.

It is certified that error appears in the above-identified patent and that said Letters Patent is hereby corrected as shown below:

In Column 11, Line 44, delete "calorimetric," and insert -- colorimetric, --, therefor.

In Column 23, Line 34, in Claim 1, delete "ananalyte" and insert -- an analyte --, therefor.

In Column 23, Line 50, in Claim 1, delete "poly(benizimidazoles)," and insert -- poly(benzimidazoles) --, therefor.

In Column 24, Line 32, in Claim 5, delete "polynrethaneureas" and insert -- polyurethaneureas --, therefor.

Signed and Sealed this

Thirtieth Day of June, 2009

JOHN DOLL
*Acting Director of the United States Patent and Trademark Office*